(12) United States Patent
Hausmann et al.

(10) Patent No.: US 8,883,168 B2
(45) Date of Patent: Nov. 11, 2014

(54) MODULATION OF IMMUNE RESPONSES BY THE POXVIRAL K4 PROTEIN

(75) Inventors: Jürgen Hausmann, Gundelfingen (DE); Hubertus Hochrein, Munich (DE); Christine Meisinger-Henschel, Neuried (DE)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 13/883,529

(22) PCT Filed: Nov. 7, 2011

(86) PCT No.: PCT/EP2011/005584
§ 371 (c)(1),
(2), (4) Date: May 3, 2013

(87) PCT Pub. No.: WO2012/059243
PCT Pub. Date: May 10, 2012

(65) Prior Publication Data
US 2013/0230553 A1 Sep. 5, 2013

Related U.S. Application Data

(60) Provisional application No. 61/410,427, filed on Nov. 5, 2010.

(51) Int. Cl.
| | | |
|---|---|---|
| *A61K 39/275* | (2006.01) | |
| *A61K 39/285* | (2006.01) | |
| *C12N 7/00* | (2006.01) | |
| *C12N 7/01* | (2006.01) | |
| *C12N 15/863* | (2006.01) | |
| *G01N 33/50* | (2006.01) | |
| *C07K 14/005* | (2006.01) | |
| *C12N 15/86* | (2006.01) | |
| *C12N 15/113* | (2010.01) | |
| *A61K 39/39* | (2006.01) | |
| *A61K 39/00* | (2006.01) | |

(52) U.S. Cl.
CPC ........ *C12N 7/00* (2013.01); *C12N 2710/24143* (2013.01); *G01N 33/5008* (2013.01); *A61K 39/285* (2013.01); *C12N 2710/24132* (2013.01); *C07K 14/005* (2013.01); *C12N 2710/24134* (2013.01); *C12N 15/86* (2013.01); *C12N 2310/14* (2013.01); *C12N 2710/24122* (2013.01); *C12N 2710/24171* (2013.01); *C12N 15/1131* (2013.01); *A61K 2039/5256* (2013.01); *A61K 39/39* (2013.01)

USPC ........... 424/199.1; 424/205.1; 424/232.1; 435/235.1; 435/320.1; 435/471

(58) Field of Classification Search
CPC ... A61K 39/285; A61K 39/39; A61K 39/275; C12N 2710/24122; C12N 2710/24132; C12N 2710/24134; C12N 2710/24143; C12N 7/00
See application file for complete search history.

(56) References Cited

FOREIGN PATENT DOCUMENTS

WO WO 03/088994 A2 10/2003
WO WO 2011/128704 A1 10/2011

OTHER PUBLICATIONS

Eckert et al (Journal of Virology 79:15084-15090, 2005, in IDS).*
Antoine et al (Virology 244:365-395, 1998) (in IDS).*
Turner et al (Journal of Virology 66:2076-2085, 1992) (in IDS).*
Blasco et al (Journal of Virology 65:5910-5920, 1991) (in IDS).*
Eckert et al (Journal of Virology 15084-15090, 2005) (in IDS).*
G. Antoine et al., "The Complete Genomic Sequence of the Modified Vaccinia Ankara Strain: Comparison with Other Orthopoxviruses," *Virol.* 244:365-395 (1998).
R. Blasco et al., "Extracellular vaccinia virus formation and cell-to-cell virus transmission are prevented by deletion of the gene encoding the 37,000-Dalton outer envelope protein," *J. Virol.* 65(11):5910-5920 (1991).
D. Eckert et al., "Vaccinia Virus Nicking-Joining Enzyme Is Encoded by K4L (VACWR035)," *J. Virol.* 79(24):15084-15090 (2005).
P.C. Turner et al., "An orthopoxvirus serpinlike gene controls the ability of infected cells to fuse," *J. Virol.* 66(4):2076-2085 (1992).
Z. Waibler et al., "Modified Vaccinia Virus Ankara Induces Toll-Like Receptor-Independent Type I Interferon Responses," *J. Virol.* 81(22):12102-12110 (2007).
Written Opinion of the International Searching Authority for International Application No. PCT/EP2011/005584, mailed Jul. 9, 2012.
International Search Report for International Application No. PCT/EP2011/005584, mailed Jul. 9, 2012.

* cited by examiner

*Primary Examiner* — Mary E Mosher
(74) *Attorney, Agent, or Firm* — Law Office of Salvatore Arrigo and Scott Lee, LLP

(57) ABSTRACT

The present invention relates to compositions, methods, and uses involving the modulation of K4 protein activity, especially in the treatment of various diseases and in the enhancement of vaccination regimens. The invention relates to poxviruses having reduced or increased K4 protein activity, as well as methods of making and using these poxviruses. The invention further relates to K4 proteins and inhibitors of K4 protein activity, as well as methods for making and using them.

28 Claims, 8 Drawing Sheets

A

B

- □ CVA-del-B19 1xE07 TCID50
- ■ CVA-del-B19 5xE07 TCID50
- ◇ CVA-del-K4/B19 1xE07 TCID50
- ◆ CVA-del-K4/B19 5xE07 TCID50

SEQUENCE LISTING

<160> NUMBER OF SEQ ID NOS: 6

<210> SEQ ID NO 1
<211> LENGTH: 1275
<212> TYPE: DNA
<213> ORGANISM: Poxvirus
<220> FEATURE:
<223> OTHER INFORMATION: K4L gene of VACV-WR-035

<400> SEQUENCE: 1
atgaatccgg ataatacaat cgcagtgatt acagagacta ttcctatagg tatgcaattt      60

-continued

```
gataaagtat atttgtctac atttaacatg tggagggaaa ttctatccaa taccacaaaa    120
acactagata tatcatcttt ttattggagt ttatcggatg aagtgggtac gaatttcggc    180
acgataatat taaacaagat tgtacaatta cccaaaagag gagtacgagt tagagtagcc    240
gtcaataaat ctaacaaacc attaaaggat gttgaaagac tacaaatggc cggagttgaa    300
gtacgataca tagatattac aaatatccta ggaggagttc ttcatacaaa attttggata    360
tctgataata cacatattta tttaggaagc gctaacatgg attggagatc actaactcag    420
gtcaaagaat gggtattgc gatcttcaat aataggaact tggcagcgga tctcactcaa    480 attttgagg tatactggta tcttggagtt aacaatctac catataattg gaaaaacttt    540
tatccgtcgt attataatac agatcatcct cttagtatta acgtaagcgg cgttccacac    600
tctgtattta ttgcttctgc accgcaacaa ctatgtacta tggaaagaac caatgattta    660
accgctttat tgtcatgtat cagaaatgcg agtaaattcg tttatgtatc tgttatgaac    720
tttatcccta ttatttattc gaaggcaggc aatattttgt tttggcctta tagaagat     780 gaattaagaa gagccgctat agacagacaa gtgtcagtta agctattgat tagttgctgg    840
caacgatctt cgtttatcat gagaaacttt ttaagatcta tcgctatgct aaaatctaaa    900
aacataaata tagaagtaaa gctatttatt gtaccagatg ctgatcctcc cattccgtat    960
tctagggtaa accatgccaa atatatggta accgataaaa cggcgtatat aggtacctca   1020
aattggacag gaaattactt tacggataca tgtggagcat ctattaatat tacaccggat   1080
gatggattag gtcttcgtca acaattggaa gatattttta tgcgtgattg gaattcaaaa   1140
tacagctatg aattgtacga tactagtcct actaaaaggt gtagactatt aaaaaatatg   1200
aaacaatgta caaatgatat atactgcgat gagatacaac cggaaaaaga aattcctgaa   1260
tattctcttg aataa                                                    1275
```

<210> SEQ ID NO 2
<211> LENGTH: 424
<212> TYPE: PRT
<213> ORGANISM: Poxvirus
<220> FEATURE:
<223> OTHER INFORMATION: K4 protein of VACV-WR-035

<400> SEQUENCE: 2

```
Met Asn Pro Asp Asn Thr Ile Ala Val Ile Thr Glu Thr Ile Pro Ile
1               5                   10                  15

Gly Met Gln Phe Asp Lys Val Tyr Leu Ser Thr Phe Asn Met Trp Arg
            20                  25                  30

Glu Ile Leu Ser Asn Thr Thr Lys Thr Leu Asp Ile Ser Ser Phe Tyr
        35                  40                  45

Trp Ser Leu Ser Asp Glu Val Gly Thr Asn Phe Gly Thr Ile Ile Leu
    50                  55                  60

Asn Lys Ile Val Gln Leu Pro Lys Arg Gly Val Arg Val Arg Val Ala
65                  70                  75                  80

Val Asn Lys Ser Asn Lys Pro Leu Lys Asp Val Glu Arg Leu Gln Met
                85                  90                  95

Ala Gly Val Glu Val Arg Tyr Ile Asp Ile Thr Asn Ile Leu Gly Gly
            100                 105                 110

Val Leu His Thr Lys Phe Trp Ile Ser Asp Asn Thr His Ile Tyr Leu
        115                 120                 125

Gly Ser Ala Asn Met Asp Trp Arg Ser Leu Thr Gln Val Lys Glu Leu
    130                 135                 140
```

```
Gly Ile Ala Ile Phe Asn Asn Arg Asn Leu Ala Ala Asp Leu Thr Gln
145                 150                 155                 160

Ile Phe Glu Val Tyr Trp Tyr Leu Gly Val Asn Asn Leu Pro Tyr Asn
                165                 170                 175

Trp Lys Asn Phe Tyr Pro Ser Tyr Tyr Asn Thr Asp His Pro Leu Ser
            180                 185                 190

Ile Asn Val Ser Gly Val Pro His Ser Val Phe Ile Ala Ser Ala Pro
        195                 200                 205

Gln Gln Leu Cys Thr Met Glu Arg Thr Asn Asp Leu Thr Ala Leu Leu
    210                 215                 220

Ser Cys Ile Arg Asn Ala Ser Lys Phe Val Tyr Val Ser Val Met Asn
225                 230                 235                 240

Phe Ile Pro Ile Ile Tyr Ser Lys Ala Gly Asn Ile Leu Phe Trp Pro
                245                 250                 255

Tyr Ile Glu Asp Glu Leu Arg Arg Ala Ala Ile Asp Arg Gln Val Ser
            260                 265                 270

Val Lys Leu Leu Ile Ser Cys Trp Gln Arg Ser Ser Phe Ile Met Arg
        275                 280                 285

Asn Phe Leu Arg Ser Ile Ala Met Leu Lys Ser Lys Asn Ile Asn Ile
    290                 295                 300

Glu Val Lys Leu Phe Ile Val Pro Asp Ala Asp Pro Pro Ile Pro Tyr
305                 310                 315                 320

Ser Arg Val Asn His Ala Lys Tyr Met Val Thr Asp Lys Thr Ala Tyr
                325                 330                 335

Ile Gly Thr Ser Asn Trp Thr Gly Asn Tyr Phe Thr Asp Thr Cys Gly
            340                 345                 350

Ala Ser Ile Asn Ile Thr Pro Asp Asp Gly Leu Gly Leu Arg Gln Gln
        355                 360                 365

Leu Glu Asp Ile Phe Met Arg Asp Trp Asn Ser Lys Tyr Ser Tyr Glu
    370                 375                 380

Leu Tyr Asp Thr Ser Pro Thr Lys Arg Cys Arg Leu Leu Lys Asn Met
385                 390                 395                 400

Lys Gln Cys Thr Asn Asp Ile Tyr Cys Asp Glu Ile Gln Pro Glu Lys
                405                 410                 415

Glu Ile Pro Glu Tyr Ser Leu Glu
            420

<210> SEQ ID NO 3
<211> LENGTH: 1275
<212> TYPE: DNA
<213> ORGANISM: Poxvirus
<220> FEATURE:
<223> OTHER INFORMATION: MVA K4L homolog gene sequence

<400> SEQUENCE: 3
atgaatccgg ataatacaat cgcagtgatt acagagacta ttcctatagg tatgcaattt      60
gataaagtat atttgtctac atttaacatg tggagggaaa ttctatccaa taccacaaaa     120
acactagata tatcatcttt ttattggagt ttatcggatg aagtgggtac gaatttcggc     180
acgataatat taaacgagat tgtacaatta cccaaaagag gagtacgagt tagagtagcc     240
gtcaataaat ctaacaaacc attaaaggat gttgaaagac tacaaatggc cggagttgaa     300
gtacgataca tagatattac aaatatccta ggaggagttc ttcatacaaa attttggata     360
tctgataata cacatatttta tttaggaagc gctaacatgg attggagatc actaactcag     420
```

```
gtcaaagaat tgggtattgc gatcttcaat aataggaact tggcagcgga tctcactcaa    480 attttgagg tatactggta tcttggagtt aacaatctac catataattg gaaaacttt      540 tatccgtcgt attataatac agatcatcct cttagtatta acgtaagtgg tgttccacac    600
tctgtattta ttgcttctgc accgcaacaa ctatgtacta tggaaagaac caatgattta    660
accgctttat tgtcatgtat tagaaatgcg agtaaattcg tttatgtatc tgttatgaac    720
tttatcccta ttatttattc gaaggcgggt aaaattttgt tttggcctta tagaaagat    780 gaattaagaa gatccgctat agacagacaa gtatccgtta agctattgat tagttgctgg    840
caacgatctt cgtttatcat gagaaacttt ttaagatcta tcgctatgct aaaatctaaa    900
aacataaata tagaagtaaa gctatttatt gtaccagatg ctgatcctcc cattccgtat    960
tctagggtaa accatgccaa atatatggta accgataaaa cggcctatat aggtacctca    1020
aattggacag gaaattactt tacggataca tgtggagcat ctattaatat tacaccggat    1080
gatggattag gtcttcgtca acaattagaa gatattttta tgcgtgattg gaattcaaaa    1140
tacagctatg aattgtacga tactagtcct actaaaaggt gtaaactatt aaaaaatatg    1200
aaacaatgta caaatgatat atactgcgat gagatacaac cggaaaaaga aattcctgaa    1260
tattctcttg aataa                                                      1275

<210> SEQ ID NO 4
<211> LENGTH: 424
<212> TYPE: PRT
<213> ORGANISM: Poxvirus
<220> FEATURE:
<223> OTHER INFORMATION: MVA K4 homolog am

```
Gln Gln Leu Cys Thr Met Glu Arg Thr Asn Asp Leu Thr Ala Leu Leu
    210                 215                 220

Ser Cys Ile Arg Asn Ala Ser Lys Phe Val Tyr Val Ser Val Met Asn
225                 230                 235                 240

Phe Ile Pro Ile Ile Tyr Ser Lys Ala Gly Lys Ile Leu Phe Trp Pro
                245                 250                 255

Tyr Ile Glu Asp Glu Leu Arg Arg Ser Ala Ile Asp Arg Gln Val Ser
                260                 265                 270

Val Lys Leu Leu Ile Ser Cys Trp Gln Arg Ser Ser Phe Ile Met Arg
            275                 280                 285

Asn Phe Leu Arg Ser Ile Ala Met Leu Lys Ser Lys Asn Ile Asn Ile
290                 295                 300

Glu Val Lys Leu Phe Ile Val Pro Asp Ala Asp Pro Pro Ile Pro Tyr
305                 310                 315                 320

Ser Arg Val Asn His Ala Lys Tyr Met Val Thr Asp Lys Thr Ala Tyr
                325                 330                 335

Ile Gly Thr Ser Asn Trp Thr Gly Asn Tyr Phe Thr Thr Cys Gly
                340                 345                 350

Ala Ser Ile Asn Ile Thr Pro Asp Asp Gly Leu Gly Leu Arg Gln Gln
                355                 360                 365

Leu Glu Asp Ile Phe Met Arg Asp Trp Asn Ser Lys Tyr Ser Tyr Glu
370                 375                 380

Leu Tyr Asp Thr Ser Pro Thr Lys Arg Cys Lys Leu Leu Lys Asn Met
385                 390                 395                 400

Lys Gln Cys Thr Asn Asp Ile Tyr Cys Asp Glu Ile Gln Pro Glu Lys
                405                 410                 415

Glu Ile Pro Glu Tyr Ser Leu Glu
                420

<210> SEQ ID NO 5
<211> LENGTH: 1056
<212> TYPE: DNA
<213> ORGANISM: Poxvirus
<220> FEATURE:
<223> OTHER INFORMATION: VACV-WR-200 = VACV-WR-B18R = VACV-B19R gene

<400> SEQUENCE: 5
atgacgatga aaatgatggt acatatatat ttcgtatcat tattgttatt gctattccac     60
agttacgcca tagacatcga aaatgaaatc acagaattct tcaataaaat gagagatact    120
ctaccagcta aagactctaa atggttgaat ccagcatgta tgttcggagg cacaatgaat    180
gatatagccg ctctaggaga gccattcagc gcaaagtgtc ctcctattga agacagtctt    240
ttatcgcaca gatataaaga ctatgtggtt aaatgggaaa ggctagaaaa aaatagacgg    300
cgacaggttt ctaataaacg tgttaaacat ggtgatttat ggatagccaa ctatacatct    360
aaattcagta accgtaggta tttgtgcacc gtaactacaa agaatggtga ctgtgttcag    420
ggtatagtta gatctcatat tagaaaacct ccttcatgca ttccaaaaac atatgaacta    480
ggtactcatg ataagtatgg catagactta tactgtggaa ttctttacgc aaaacattat    540
aataatataa cttggtataa agataataag gaaattaata tcgacgacat taagtattca    600
caaacgggaa aggaattaat tattcataat ccagagttag aagatagcgg aagatacgac    660
tgttacgttc attacgacga cgttagaatc aagaatgata tcgtagtatc aagatgtaaa    720
atacttacgg ttataccgtc acaagaccac aggtttaaac taatactaga tccaaaaatc    780
aacgtaacga taggagaacc tgccaatata acatgcactg ctgtgtcaac gtcattattg    840
```

-continued

```
attgacgatg tactgattga atgggaaaat ccatccggat ggcttatagg attcgatttt      900
gatgtatact ctgttttaac tagtagaggc ggtattaccg aggcgacctt gtactttgaa      960
aatgttactg aagaatatat aggtaataca tataaatgtc gtggacacaa ctattatttt     1020
gaaaaaaccc ttacaactac agtagtattg gagtaa                                1056
```

```
<210> SEQ ID NO 6
<211> LENGTH: 351
<212> TYPE: PRT
<213> ORGANISM: Poxvirus
<220> FEATURE:
<223> OTHER INFORMATION: VACV-WR-B18 = VACV-B19 protein

<400> SEQUENCE: 6
```

Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
            20                  25                  30

Phe Phe Asn Lys Met Arg Asp Thr Leu Pro Ala Lys Asp Ser Lys Trp
        35                  40                  45

Leu Asn Pro Ala Cys Met Phe Gly Gly Thr Met Asn Asp Ile Ala Ala
    50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95

Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
    130                 135                 140

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
            180                 185                 190

Asn Ile Asp Asp Ile Lys Tyr Ser Gln Thr Gly Lys Glu Leu Ile Ile
        195                 200                 205

His Asn Pro Glu Leu Glu Asp Ser Gly Arg Tyr Asp Cys Tyr Val His
    210                 215                 220

Tyr Asp Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
            260                 265                 270

Thr Ala Val Ser Thr Ser Leu Leu Ile Asp Asp Val Leu Ile Glu Trp
        275                 280                 285

Glu Asn Pro Ser Gly Trp Leu Ile Gly Phe Asp Phe Asp Val Tyr Ser
    290                 295                 300

Val Leu Thr Ser Arg Gly Gly Ile Thr Glu Ala Thr Leu Tyr Phe Glu
305                 310                 315                 320

-continued

```
Asn Val Thr Glu Glu Tyr Ile Gly Asn Thr Tyr Lys Cys Arg Gly His
            325                 330                 335

Asn Tyr Tyr Phe Glu Lys Thr Leu Thr Thr Thr Val Val Leu Glu
            340                 345             350
```

MODULATION OF IMMUNE RESPONSES BY THE POXVIRAL K4 PROTEIN

The present invention relates to a poxviral K4 protein and poxviral K4L gene as a target or tool for modulating immune responses. In one aspect, the present invention relates to an enhancement of immune responses by reducing K4 protein activity. In particular, the present invention relates to poxviruses having reduced K4 protein activity and, optionally, reduced B19 protein activity. In a further aspect, the present invention relates to a reduction of immune responses by enhancing K4 protein activity. The present invention additionally relates to methods for generating such poxviruses, to pharmaceutical compositions comprising the same as well as to medical and non-medical uses thereof.

BACKGROUND OF THE INVENTION

The immune system recognizes pathogens, including viruses, by means of pattern recognition receptors (PRRs). Among the PRRs is the family of toll-like receptors (TLRs), RIG-like helicases (RLHs) as well as nucleotide-binding domain- and leucine-rich repeat-containing molecules (NLRs). Activation of PRRs leads to the activation of immune cells including dendritic cells (DCs) and the induction of innate and adaptive immune responses.

The development of new viral-based vaccines requires viral strains which exhibit a unique combination of characteristics. First, the virus used as a delivery vector in the vaccine is generally engineered, at the level of its genome, to comprise the coding sequence of one or more foreign antigens (a protein not expressed by the wild-type virus) against which an immune response is desired. In its expressed form, the foreign antigen presented to the subject to be immunized is generally a protein of the pathogen that causes the disease which vaccination is intended to treat or prevent. However, the foreign antigen can also be a host antigen, such as a tumor antigen. Upon delivery into target cells within the individual to be vaccinated, the sequence encoding the foreign antigen is expressed as the corresponding protein, and this protein then is recognized by the individual's immune system, which then mounts the desired immune response against the foreign antigen, enhancing the host's ability to specifically combat the disease caused by the pathogen from which the foreign antigen was taken. This intended mode of action means that viral strains suitable for use in vector vaccination strategies against a heterologous pathogen must retain their ability to infect host cells. At the same time, however, such viral strains should be attenuated in their own replicative behavior, so that they do not themselves replicate within the individual's host cell. They should also themselves be non-pathogenic.

A virus which has been engineered to comprise the coding sequence of a foreign antigen of interest, but which is not attenuated in its replication and/or pathogenicity may cause significant disease, possibly undermining the intended vaccination strategy. Therefore, the vector vaccine should be as attenuated as possible to prevent induction of disease and limit severe adverse effects. A virus which is attenuated in its own replication and/or pathogenicity, but which is not sufficiently immunogenic may deliver the sequence encoding the foreign antigen of choice to the individual's immune system, but is not likely to engender the desired immunogenic response against this antigen, thereby once again undermining the effectiveness of the vaccination strategy. Thus, the vaccine must elicit production of enough of the foreign antigen(s) to present to the host immune system so that the desired immune response is triggered. In addition, the vaccine must not suppress the host's immune system to induce a fast and highly effective immune response. At the same time, the host immune system must also itself be sensitive enough to react to the amount of foreign antigen produced by the vaccine.

The vaccinia virus K4L gene encodes a DNA nicking-joining enzyme (Eckert et al. 2005). Eckert et al. found that there were no significant differences between a wild-type vaccinia virus (Western Reserve, WR) and a corresponding vaccinia virus lacking K4L with respect to infectivity, growth characteristics, or processing of viral replicative intermediate DNA, including both telomeric and cross-linked forms.

The vaccinia virus B19R gene described in Symons et al. 1995 encodes a protein binding type I interferons (IFN-alphas/betas), thus neutralizing the biological activity of these type I interferons. All genes of vaccinia virus WR (VACV) mentioned in this report are designated using the names of their orthologue in the VACV strain Copenhagen (VACV-Cop) according to the VACV-Cop gene notation system (Rosel et al. 1986; Goebel et al. 1990). This also applies to VACV-WR genes that are referred to in the literature applying the nomenclature system now reserved for VACV-Cop orthologues due to strain variations in gene content and topology. For example, the gene encoding the VACV interferon type I-biding protein has historically been named B18R in the VACV-WR strain. The orthologue of this gene in the VACV-Cop is named B19R, and we thus refer to this gene as B19R in this application.

It is thus an object of the present invention to provide improved vaccines and vaccination strategies. It is a further object of the invention to provide treatment strategies for various diseases which are caused by excessive interferon and cytokine induction due to aberrant stimulation of TLR9 or other DNA recognition molecules of the innate immune system.

SUMMARY OF THE INVENTION

The present invention relates to poxviruses that have reduced K4 protein activity, including a complete lack of K4 protein activity. Preferably, the poxvirus is an orthopoxvirus other than vaccinia virus Western Reserve (WR) or a capripoxvirus. The poxvirus can be a virus that has reduced B19 protein activity, such as MVA or one in which the B19 gene or its homologue is subjected to mutagenesis. Preferably, the poxvirus is a recombinant poxvirus. The invention further relates to the genomes of these poxviruses and nucleic acids comprising these genomes.

The invention encompasses methods for generating poxviruses that do not express a K4 protein or express a K4 protein with reduced, or no, K4 protein activity relative to the wild-type protein. The invention further encompasses methods for inducing the production of IFN-α and IFN-λ with these poxviruses.

The invention further relates to immunogenic compositions and vaccines comprising such poxviruses as well as methods for preparing such immunogenic compositions and vaccines. The invention further relates to uses of the above products for enhancing the immune response against a foreign antigen in a vaccination regimen and for inducing or enhancing the production of IFN-α and IFN-λ.

The invention further relates to screening methods for determining whether or not a substance is an inhibitor of a poxviral K4 protein. The present invention further relates to these inhibitors, processes for preparing an inhibitor of a poxviral K4 protein, and uses of such inhibitors as a medicament in general, as well as a medicament in the treatment of an infectious viral disease.

The invention further relates to a poxvirus encoding a K4 protein with enhanced activity relative to wild-type protein. The invention further relates to a vector, particularly a viral vector, which encodes a functional K4 protein. The invention further relates to such vectors for use as a medicament in general, as well as for use as a medicament for the treatment and/or prevention of a disease characterized by an excessive immune response involving a toll-like receptor 9 (TLR9)-dependent pathway. The invention further relates to a poxviral K4 protein for use as a medicament in general, as well as for use as a medicament for the treatment and/or prevention of a disease characterized by an excessive immune response involving a toll-like receptor 9 (TLR9)-dependent pathway. The invention further relates to a poxvirus encoding K4 protein activity for use as a medicament for the treatment and/or prevention of a disease characterized by an excessive immune response involving a toll-like receptor 9 (TLR9)-dependent pathway. The invention further relates to a poxviral K4 protein, viral vectors or a poxvirus encoding K4 protein activity for use as medicaments for enhancing expression of a foreign protein.

DETAILED DESCRIPTION OF THE INVENTION

The inventors have surprisingly found that poxviruses which do not express a functional K4 protein are capable of eliciting a stronger immune response when used as part of a viral vaccination strategy than poxviruses which express a functional K4 protein. Poxviruses without functional K4 protein unexpectedly increase the activity of the host immune system. These results indicate that a more potent vaccination effect may be achieved with vaccines and viruses of the present invention than with other known vaccines and viruses administered in equivalent amounts and/or which express equivalent amounts of foreign antigen.

Specifically, the inventors have identified the K4 protein as an inhibitor of pathways required for IFN-alpha induction in plasmacytoid dendritic cells (pDC). pDC are selectively competent to produce large amounts of IFN type-I (IFN-alphas/betas) and type-III (IFN-lambdas) in response to TLR7/8 or -9 stimulation. A poxviral K4L gene deletion mutant surprisingly induced more pDC-dependent IFN-alpha than wild-type virus, and the mutant not only produced more IFN-alpha, but also induced more IFN-lambda. IFN-alphas and -lambdas are highly active in virus inhibition. Usually, detection of poxviral DNA by immune cells via TLR9 leads to production of type-I and type-III interferons. In addition, expression of NF-kappa-B-driven cytokine genes was increased by K4L deletion mutants. The inventors have surprisingly found that, under normal conditions, viral DNA is modified to escape or inhibit recognition by TLR9 and pDC as well as other cell types utilizing the TLR9 receptor. This represents a mechanism of viral immune suppression which has not been observed previously. Furthermore, the K4L gene and/or the K4L gene product has not been previously described as an immune suppressive or virulence factor.

Poxviruses

The invention encompasses poxviruses that have reduced, or increased, K4 protein activity, including a complete lack of K4 protein activity. The poxvirus can also have reduced B19 protein activity.

The poxvirus is preferably a capripoxvirus or an orthopoxvirus. The orthopoxvirus may preferably be vaccinia virus, cowpox virus, ectromelia virus, monkeypox virus, taterapox virus, or camelpox virus.

Preferably, the orthopoxvirus is a vaccinia virus (VACV), a chorioallantois vaccinia virus Ankara (CVA), or a modified vaccinia virus Ankara (MVA), particularly, MVA 575, MVA572, or MVA-BN.

MVA-572 was deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 0JG, United Kingdom, as ECACC V94012707. MVA-575 was deposited on Dec. 7, 2000, at the ECACC with the deposition number V00120707. MVA-BN was deposited on Aug. 30, 2000 at the ECACC under number V00083008.

Recombinant Poxviruses

The invention encompasses recombinant poxviruses comprising foreign nucleic acid incorporated in a variety of insertion sites in the poxviral genome. The foreign nucleic acid can encode a foreign protein(s) and/or foreign antigen(s), such as viral antigens, bacterial antigens, and human tumor associated antigens. Preferably, the foreign antigen is selected from retroviridae, paramyxoviridae, orthorthomyxoviridae, bunyaviridae, flaviviridae, filoviridae, picornaviridae, rhabdoviridae, bornaviridae, coronaviridae, caliciviridae, arenaviridae, togaviridae, reoviridae, arteviridae, astroviridae, poxviridae, herpesviridae, adenoviridae, papillomaviridae, polyomaviridae, hepadnaviridae, parvoviridae, and anelloviridae as well as from *Bacillus anthracis* or other bacterial pathogens, and from PAP, PSA, 5T4, MUC, and p53 antigens.

As used herein, a "foreign" gene, nucleic acid, antigen, or protein is understood to be a nucleic acid or amino acid sequence which is not present in the wild-type poxvirus. The skilled person understands that a "foreign gene", when present in a poxvirus, is to be incorporated into the poxviral genome in such a way that, following administration of this poxvirus to a host cell, it is expressed as the corresponding foreign gene product, i.e. as the "foreign antigen" \or "foreign protein." Expression is normally achieved by operatively linking the foreign gene to regulatory elements that allow expression in the poxvirus-infected cell. Preferably, the regulatory elements include a natural or synthetic poxviral promoter. In this way, the antigenic determinants of the foreign antigen can be delivered to the host immune system which is able to mount an immune response against the foreign antigen.

The foreign genes can be inserted into the recombinant poxvirus, preferably MVA virus as separate transcriptional units or as fusion genes. A further aspect relates to a poxvirus comprising one or more foreign genes and expressing reduced K4 and/or reduced B19 protein activity.

A further aspect of the invention provides a vector comprising a genome of the poxvirus described above. In some embodiments, the vector is a plasmid.

In one embodiment, the foreign nucleic acid is inserted into an intergenic region(s) of an MVA. In preferred embodiments, the intergenic region (IGR) is selected from IGR07/08, IGR 44/45, IGR 64/65, IGR 88/89, IGR 136/137, and IGR 148/149. In one embodiment, the foreign nucleic acid is inserted into naturally occurring deletion site(s) I, II, II, IV, V, or VI of the MVA.

The recombinant poxvirus, preferably MVA virus can be generated by routine methods known in the art. Methods to obtain recombinant poxviruses or to insert exogenous coding sequences into a poxviral genome are well known to the person skilled in the art. For example, methods are described in the following references: Molecular Cloning, A laboratory Manual. Second Edition. By J. Sambrook, E. F. Fritsch and T. Maniatis. Cold Spring Harbor Laboratory Press. 1989: describes techniques for standard molecular biology techniques such as cloning of DNA, DNA and RNA isolation, western blot analysis, RT-PCR and PCR amplification techniques. Virology Methods Manual. Edited by Brian W. J. Mahy and Hillar O Kangro. Academic Press. 1996: describes techniques for the handling and manipulation of viruses. Molecular Virology: A Practical Approach. Edited by A. J. Davison and R. M. Elliott. The Practical Approach Series. IRL Press at Oxford University Press. Oxford 1993. Chapter 9: Expression of genes by Vaccinia virus vectors. Current Protocols in Molecular Biology. Publisher: John Wiley and Son Inc. 1998. Chapter 16, section IV: Expression of proteins in mammalian cells using vaccinia viral vector: describes techniques and know-how for the handling, manipulation and genetic engineering of MVA.

For the generation of recombinant poxviruses according to the present invention, different methods may be applicable. The DNA sequence to be inserted into the virus can be placed into an *E. coli* plasmid construct into which DNA homologous to a section of the poxvirus DNA genome has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a non-essential locus in the poxviral DNA. The resulting plasmid construct can be amplified by propagation within *E. coli* bacteria and isolated. The isolated plasmid containing the DNA gene sequence to be inserted can be transfected into a cell culture, e.g., chicken embryo fibroblasts (CEFs), along with infection of this culture by the poxvirus. Recombination between homologous poxviral DNA sequences in the plasmid and the viral genome, respectively, can generate a poxvirus modified by the presence of foreign DNA sequences.

According to a preferred embodiment, a cell of a suitable cell culture as, e.g., CEF cells, can be infected with a poxvirus. The infected cell can be, subsequently, transfected with a first plasmid vector comprising a foreign gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign gene or genes. In case, this gene can be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, coinfect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E.coli* or another bacterial species between a vaccinia virus genome cloned as a bacterial artificial chromosome (BAC) and a linear foreign sequence flanked with DNA sequences homologous to sequences flanking the desired site of integration in the vaccinia virus genome.

K4L Gene and K4 Protein

As used herein, a “K4L gene” is the gene designated by VACWR035 in e.g. Eckert et al. 2005 describing the K4L gene in the Western Reserve (WR) strain of vaccinia virus, and its homologues in other poxviral genomes having the same K4 protein enzymatic activity. In the WR strain, the K4L gene is located at nucleotides 27624-28898 (endpoints included), as numbered in GenBank accession number NC_006998. The nucleotide sequence of this K4L gene from vaccinia WR is as given in SEQ ID NO: 1. In this case, the amino acid sequence of the corresponding wild-type K4 protein from vaccinia strain WR is as set out in SEQ ID NO: 2. In certain preferred embodiments, the nucleotide sequence of the K4L gene is as given in SEQ ID NO: 3, the K4L sequence in modified vaccinia virus strain Ankara (MVA). In this case, the amino acid sequence of the corresponding wild-type K4 protein from MVA is as set out in SEQ ID NO: 4. Moreover, homologous and non-homologous genes from any other species encoding proteins with K4-like enzymatic and immunomodulatory activity are included in the term “K4L-like gene”.

The skilled person will understand that the exact sequence and location of the K4L gene in different poxviral strains may vary from of the WR K4L gene. A “K4L gene” encompasses any and all homologues of the WR K4L gene, even though the sequence and/or genomic location may be different.

As used herein, a “homologue” of the WR K4L gene refers to a gene that, when aligned by standard methods with the sequence designated by GenBank accession number NC_006998, exhibits at least 50% identity to nucleotides 27624-28898 thereof (endpoints included). As an example, the sequence corresponding to the K4L gene in MVA that has the locus name MVA025L (Antoine et al. 1998) and is located at nucleotides 16025-17299 in the MVA-BN sequence (GenBank acc. no. DQ983238.1) is a homologue of the WR K4L gene. The skilled person can easily determine this using standard in silico similarity search techniques available using established software packages, for example the protein BLAST program blastp, which is available under http://blast-.ncbi.nlm.nih.gov/ with default parameters. For example, a sequence which is not identical to K4L, will be understood as a “homologue” of the WR K4L gene. A homologue of the WR K4L gene has at least 50% identity, preferably at least 70% identity, preferably at least 75% identity, more preferably at least 80% identity, most preferably at least 90% identity to nucleotides 27624-28898 of GenBank accession number NC_006998 (SEQ ID NO: 1). Thus, the term “K4L gene” includes, but is not limited to the specific sequence given by nucleotides 27624-28898 of GenBank accession number NC_006998 (SEQ ID NO: 1).

As used herein, "K4 protein" refers to the protein product expressed by a K4L gene. As used herein, "K4 protein activity" refers to the immunosuppressive activity of K4 that can be measured by the effect of K4 on the production of immune factors by immune cells when these immune cells are appropriately stimulated. In addition, "K4 protein activity" refers to the nuclease activity attributable to the K4 protein, as described in Eckert et al. 2005. K4 protein activity can be measured by known methods, for example the nuclease assay described in Eckert et al. 2005, page 15085 thereof, left column, section titled "Nuclease assay". This section refers to a nuclease assay in which supercoiled plasmid DNA is treated with a nuclease, such as the K4 protein with nicking-joining activity, and converted by this nuclease to nicked circular (single-stranded break) and linear (double-stranded break). The respective amounts of supercoiled, nicked circular and linear DNA following reaction can be resolved by agarose gel electrophoresis, and the relative band intensities quantified by known methods (e.g. ethidium bromide staining or densitometry scan). When the K4 protein is used as the putative nuclease which is allowed to react with the supercoiled DNA, the ratio of the combined amount of nicked circular and linear DNA (reacted) to supercoiled DNA (unreacted) serves as a quantitative indication of K4 protein activity, with lower ratios indicating lower amounts of strand cleavage and thus lower amounts of K4 protein activity. Of course, other similar assays can also be used.

In order to quantify encoded K4 protein activity, one can react supercoiled DNA in a standard concentration with a standard concentration of an extract of a virus extract prepared as follows. Poxviruses can be propagated on Vero cells in the case of replication competent viruses, and on chicken embryo fibroblasts in the case of replication-restricted MVA, and purified by two consecutive centrifugations over a sucrose cushion according to standard procedures (Kotwal and Abrahams 2004). 2.5 optical density units (at 260 nm) of virus purified by centrifugation over two sucrose cushions is resuspended in 800 µl of buffer (50 mM Tris-HCl, pH 8.0, 10 mM dithiothreitol [DTT], 0.05% NP-40) and incubated on ice for 10 min. The sample is spun in e.g. a Beckman Microfuge at 13,000 rpm for 5 min. The pellet is resuspended in 150 µl of 300 mM Tris-HCl, pH 8.0, 250 mM NaCl, 0.1 mM EDTA, 50 mM DTT, 0.1% sodium deoxycholate and incubated on ice for 30 min. The sample is centrifuged in e.g. a Beckman Microfuge at 13,000 rpm for 5 min, and the supernatant is applied to an Ultrafree-MC DEAE centrifugal filter device (e.g. by Millipore) and centrifuged for 1 minute at 5,000×g, said filter device having been pre-equilibrated by the addition of 400 µl of 300 mM Tris-HCl, pH 8.0, 250 mM NaCl, 0.1 mM EDTA, 50 mM DTT, 0.1% sodium deoxycholate and centrifugation at 5,000×g for 1 minute. The eluate is stored at −20° C. after the addition of a one-quarter volume (37.5 µl) of 200 mM Tris-HCl, pH 8.0, 8 mM DTT, 4 mM EDTA, 40% glycerol. This is the viral extract which is subsequently brought into contact with the supercoiled DNA in the nuclease assay to quantify the encoded K4 protein activity.

Cytosolic extract of cells infected with viruses encoding or not encoding a functional K4 protein or Mock infected cells can be prepared by scraping the cells into the culture medium, rinsing the cells once with phosphate-buffered saline and then resuspending the cells in 0.5 to 1.0 ml of T-lysis buffer (1% Triton X-100, 150 mM NaCl, 50 mM Tris-HCl, pH 8.0. After three freeze-thaw cycles, cellular debris is spun down at 500 g and supernatants are stored at −20° C. or immediately used in the nuclease assay.

A typical nuclease assay may for instance be performed in the following manner: A reaction volume of 50 µl containing 1 µg of pECHC and 1 µl of extract in 10 mM 2-(N-morpholino)-ethanesulfonic acid, pH 6.5, 10 mM EDTA, 100 µg/ml bovine serum albumin is incubated at 55° C. for 30 min. The reaction mixtures (reference and test reactions) are cooled to room temperature and extracted three times with an equal volume of phenol, phenol-chloroform, and finally chloroform. Samples are mixed with DNA agarose dye buffer and separated by electrophoresis through neutral or alkaline agarose gels, and the gel results are quantified as indicated above.

As used herein, "wild-type K4 protein activity" denotes the activity attributable to the K4 protein prior to any mutation of the K4L gene encoding the K4 protein. For example, wild-type CVA and wild-type MVA have wild-type K4 protein activity. Similarly, recombinant forms of CVA and MVA with unmutated K4L genes have wild-type K4 protein activity. Viruses with mutations in their K4L genes may have reduced or increased K4 protein activity, relative to wild-type K4 protein activity. As one will normally begin with a virus in which the K4L gene has not yet been modified, i.e. a virus in which the K4L gene is in its wild-type form, "wild-type K4 protein activity" corresponds to the enzymatic activity of the wild-type K4 protein. Any reduction in the activity attributable to this protein caused by changes to the starting virus, when measured under equivalent assay conditions, will constitute a reduction in K4 protein activity relative to the wild-type protein. Thus, a poxvirus can encode a K4 protein with enzymatic activity that is lower than wild-type K4 protein activity, or even completely absent. This is referred to herein as reduced K4 protein activity. Conversely, a poxvirus can encode K4 protein activity which is higher than wild-type K4 protein activity. This is referred to herein as increased K4 protein activity.

Within the context of this invention, "reduced" K4 protein activity means a significant reduction in K4 protein activity. Reduced K4 protein activity includes an at least 2-fold, 5-fold, 10-fold, 20-fold, or 100-fold reduction K4 protein activity. Reduced K4 protein activity (i.e., relative to wild-type K4 protein activity) may be due to multiple factors. It may for instance be due to a lower amount of the K4 protein (the K4L gene product) being expressed. This would include mutations that remove or alter nucleic acid sequences important for transcription of the messenger RNA encoding the K4 protein or nucleic acid sequences important for translation of the K4 protein. It may also be due to a non-native, i.e. mutated K4 protein expressed in the same, or lower, amount as native K4 protein. Reduced K4 protein activity may also be due to complete deletion of a K4L gene.

Generally, to cause a poxvirus to express reduced K4 protein activity relative to wild-type K4 protein activity, it will be most expedient to simply delete the K4L gene from the respective poxvirus, so that no native K4 protein will be encoded or expressed. In this preferred case, the encoded K4 protein activity is absent, and the absence of K4 protein activity is included in the meaning of reduced K4 protein activity as set out hereinabove. However, it is also possible to introduce one or more mutations into the native K4 gene so as to yield lower amounts of functional K4 protein activity. Furthermore, it is also possible to introduce one or more mutations into the native K4 gene so as to yield, when expressed, a mutant K4 protein with reduced K4 protein activity.

The sequence of the K4 protein in vaccinia virus strain WR is as set out in SEQ ID NO: 2, and the sequence of the K4 protein in MVA is as set out in SEQ ID NO: 4. The invention includes other K4 proteins encoded by a K4L gene. Accordingly, a "K4 protein" as used herein includes, but is not limited to, homologues of SEQ ID NO: 2 and 4 having at least 50%, 60% 70%, 80%, 90% or 95% identity to SEQ ID NO: 2 or 4.

As used herein, "eliminated K4 protein activity", or "absent K4 protein activity", or "no K4 protein activity" denotes the scenario in which the poxvirus encodes no K4 protein activity, i.e. in which the K4 protein product is either absent or eliminated. Generally, this will be accomplished by the complete deletion of the K4L gene. Eliminated K4 protein activity, absent K4 protein activity, and no K4 protein activity are encompassed by the phrase "reduced K4 protein activity."

B19R Gene and B19 Protein

In certain embodiments, it may be advantageous that the poxvirus additionally lacks B19 protein activity or has reduced B19 protein activity relative to wild-type B19 protein activity. The meaning of "wild-type", "reduced", "eliminated", "absent", "no", and "increased" B19 protein activity is analogous to that explained above for K4 protein activity. The present inventors have surprisingly found that the strength of an immune response can be potentiated by administration of a poxvirus expressing a foreign antigen of interest when, in addition to reduced K4 protein activity, the poxvirus genome also has reduced B19 protein activity. As a result of this heightened immune response, a poxvirus with mutations and/or partial or total deletions in both K4L and B19R genes, i.e. a poxvirus in which the K4 protein activity and the B19 protein activity have been reduced, may engender a significantly higher immunogenic immune response against a desired antigen as compared to poxviral vectors in which the activity of both of these genes remains intact in their respective wild-type forms, engendering "wild-type K4 and B19 protein activity". Additionally, the inventors have found that a poxviral mutant in which both K4 protein activity and B19 protein activity have been reduced is significantly less virulent than a poxvirus in which the functional activity of these genes is retained.

As used herein, the "B19R gene" includes a gene as defined in Symons et al. 1995 and its homologues in other poxviral genomes having the same B19 protein enzymatic activity. The B19R gene in the vaccinia strain WR is located from nucleotides 179102-180157 (endpoints included) of the GenBank accession number NC_006998 (SEQ ID NO: 5). The corresponding sequence of the B19 protein of WR is as set out in SEQ ID NO: 6.

The skilled person will understand that the exact sequence and location of the B19R gene in different poxviral strains may vary from of the WR B19R gene. A "B19R gene" encompasses any and all homologues of the WR B19R gene, even though the sequence and/or genomic location may be different.

As used herein, a "homologue" of the VACV-WR B19R gene refers to a gene that, when aligned by standard methods with SEQ ID NO: 5 exhibits at least 50% identity to nucleotides 179102-180157 (endpoints included) of the GenBank accession number NC_006998 (SEQ ID NO: 5). The skilled person can easily determine this using standard in silico similarity search techniques available using established software packages, for example the protein BLAST program blastp, which is available under http://blast.ncbi.nlm.nih.gov/ with default parameters. For example, a sequence which is not identical to B19R, will be understood as a "homologue" of the WR B19R gene. A homologue of the WR B19R gene has at least 50% identity, preferably at least 70% identity, preferably at least 75% identity, more preferably at least 80% identity, most preferably at least 90% identity to 179102-180157 (endpoints included) of the GenBank accession number NC_006998 (SEQ ID NO: 5). Thus, the term "B19R gene" includes, but is not limited to the specific sequence given by nucleotides 179102-180157 (endpoints included) of the GenBank accession number NC_006998 (SEQ ID NO: 5).

The sequence of the B19R gene in MVA is as set out in SEQ ID NO: 7, while the sequence of the corresponding MVA B19 protein is set out in SEQ ID NO: 8. MVA encodes a truncated version of the B19 protein which is non-functional and therefore elimination of the remaining B19R nucleotide sequences in MVA is not necessary to achieve reduced B19 protein activity.

As used herein, "B19 protein" refers to the protein product expressed by a B19R gene. As used herein, "B19 protein activity" refers to the ability of B19 protein to bind to type I interferons and to neutralize secreted IFN type I in the medium, as described in Symons et al. 1995. B19 protein activity can be measured by known methods, for example the methods in Symons et al. 1995, or by other methods known to the skilled artisan.

Mutants

The K4L gene encoding functional K4 protein activity can be mutated such that the encoded K4 protein activity is reduced relative to wild-type K4 protein activity in the initial poxvirus genome. In the case that B19 protein activity is additionally to be reduced, the same applies to the B19R gene. A "mutation" refers to any change to the nucleotide sequence of the gene, including a deletion, insertion, substitution and/or inversion within the gene to be mutated. A mutation can be a single nucleotide change, such that the corresponding codon is altered to yield a different amino acid than in the non-mutated form. The same applies for an inversion; here an inversion may be as little as in two nucleotides within the respective gene. A "mutation" encompasses any combination of one or more insertions, deletions, substitutions and/or inversions.

Accordingly, it is preferred in some embodiments to mutate the K4L gene, or K4L and B19R genes, of a poxvirus genome. In various embodiments, one or both of these genes are completely or substantially deleted, leading to elimination of the corresponding protein activity. In some embodiments, the mutation is introduced into a coding region of the K4L gene, or of the K4L and B19R genes. This can have the advantage that a different amino acid sequence of the corresponding protein results, which may reduce the encoded protein activity in a readily determinable manner (see above). In other preferred embodiments, the mutation is introduced into a non-coding region of the K4L gene, or K4L and B19R genes. This can have the advantage that non-coded sequences which function in the regulation of expression of the gene(s) are modified so as to reduce the amount of functional protein product expressed. In still other preferred embodiments, mutations are introduced into both coding and non-coding regions of the K4L gene, or K4L and B19R genes. Such embodiments may have the advantage of reducing both the activity of expressed protein, as well as the overall amount of protein expressed. In this way, the K4 protein activity or K4 and B19 protein activities are reduced to below the level of wild-type K4 protein activity or wild-type K4 and B19 protein activities, respectively.

In one embodiment, the invention encompasses a method for generating a poxvirus having reduced K4 protein activity comprising introducing a mutation into a K4 gene of a poxvirus, wherein the resultant mutated poxvirus has reduced K4 protein activity. The method can further comprise introducing a mutation into a B19 gene of a poxvirus, wherein the resultant mutated poxvirus has reduced B19 protein activity. The invention further encompasses poxviruses generated by these methods and their genomic nucleic acids and encoded proteins.

Immunological Compositions, Methods of Administration, and Uses as Therapeutics

A further aspect of the invention provides immunogenic compositions and vaccines comprising: (a) the genome and/or poxvirus as described above; and, optionally, (b) a pharmaceutically acceptable carrier.

The invention includes the use of the compositions above for the induction of IFN-α and/or IFN-λ in a human patient. In one embodiment, a poxvirus is subjected to mutagenesis to reduce K4 protein activity, optionally also reducing B19 protein activity. The mutated poxviruses is then administered to the patient to induce the level of IFN-α and/or IFN-λ in the patient.

A further aspect of the invention provides a method for preparing a immunogenic composition or a vaccine comprising a poxvirus expressing one or more foreign gene products, i.e. one or more foreign antigens (a) providing a poxvirus expressing a functional K4L gene product; (b) mutating the poxvirus such that the poxvirus expresses reduced K4 protein activity compared to the corresponding wild-type poxvirus, and, optionally, (c) combining the mutated poxvirus with a pharmaceutically acceptable carrier.

A further aspect of the invention provides a poxvirus vector as set out above (i.e. one comprising a poxviral genome comprising one or more foreign genes and a genome mutated to encode a K4 protein with reduced activity compared to the activity of the K4 protein encoded by the parental poxvirus vector (wild-type K4L), or a vaccine comprising such a poxvirus, for use in the production or enhancement of an immune response against a foreign antigen in a vaccination regimen.

As used herein, a "pharmaceutically acceptable carrier" generally refers to one or more carriers, additives, antibiotics, preservatives, adjuvants, diluents and/or stabilizers which have been approved. Such auxiliary substances can for example be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

In a preferred embodiment, K4 protein activity is absent in the poxviral genome. This may most readily be effected by removing the K4L gene altogether. In another embodiment, both K4 and B19 protein activities are absent in the poxviral genome. The elimination of K4, or of K4 and B19 protein activities may be readily accomplished by standard recombinant techniques to delete the desired gene or genes.

A further aspect of the invention provides a poxvirus vector as set out above (i.e. one comprising a poxviral genome comprising a foreign gene and a genome mutated to encode reduced or absent K4 protein activity), or a vaccine comprising such a poxvirus, for use as a medicament for enhancing the immune response against a foreign antigen in a vaccination regimen. As explained above, the reduction in K4 protein activity in poxviruses leads to an unexpected potentiation of the host immune response when such poxviruses are used as part of a vaccination regimen. Preferably, the poxviruses may be used as the vector with which a foreign antigen is delivered to the individual to be vaccinated. The increased activation of the host immune system by the reduction or elimination of K4 protein activity allows a more potent immune response to be mounted than would be possible if K4 was present. This advantageously strengthens the achievable vaccination effect. Thus, this opens up vaccination strategies which have previously been deemed too inefficient.

Inhibitors of K4 Protein Activity

Having established the surprising role of the K4 protein in sensitizing the immune system, the inventors have advantageously extended this finding to the potential treatment of diseases in which existing K4 protein activity, such as that engendered by poxviruses upon infection of a host in order to evade recognition by the host immune system, is reduced or eliminated by applying an inhibitor of the K4 protein product. Inhibiting the activity of already present K4 protein can potentiate the immune response against an invading pathogenic poxvirus. However, in the case of a disease caused by a poxvirus, is it clear that the K4 activity cannot be altered in the manner described above for poxviral-based vaccines, since the virus here is the infecting entity. In this case, suppressing K4 activity must then be achieved by administration of an external substance, i.e. an inhibitor of a K4 protein activity.

The invention encompasses inhibitors of K4 protein activity. An inhibitor of K4 protein is a compound that can cause reduced K4 protein activity when incubated with the K4 protein in vivo or in vitro. Reduced K4 protein activity includes an at least 2-fold, 5-fold, 10-fold, 20-fold, or 100-fold reduction of K4 protein activity. These include small molecule inhibitors, antibodies which specifically bind to a poxviral K4 protein, and nucleic acid inhibitors, such as decoy nucleic acids that irreversibly bind to K4 protein, antisense RNAs, ribozymes, and siRNAs.

The inhibitor is preferably in a pharmaceutical composition. In preferred embodiments, the inhibitor is "isolated and purified", that is, essentially free of association with other host DNA, proteins, or polypeptides, for example, as a purification product of recombinant host cell culture or as a purified product from a non-recombinant source.

The invention encompasses methods of determining whether or not a substance is an inhibitor of a poxviral K4 protein, comprising any combination or all of the following steps:

(i) Adding or not adding the test substance in a nuclease assay using virion extracts with known K4 protein activity;
(ii) Measuring the level of nicking and/or linearization of target plasmid in the absence of the test substance, thereby resulting in a first factor level;
(iii) Measuring the level of nicking and/or linearization of the same target plasmid in the presence of the test substance, thereby resulting in a second factor level;
(iv) Subtracting the first factor level from the second factor level to provide a difference factor level;
(v) Determining, if the difference factor level is positive, that the test substance is an inhibitor of the poxviral K4 protein or, if the difference factor level is not positive, that the test substance is not an inhibitor of the poxviral K4 protein.
(a) Providing a test substance suspected of being an inhibitor of the poxviral K4 protein;
(b) Infecting a dendritic cell (DC) with a poxvirus having K4 protein activity;
(c) Measuring the level of an immune factor produced by the infected DC in the absence of the test substance for both infected DC samples, thereby resulting in two first factor levels;
(d) Measuring the level of the same immune factor as in (c) produced by both infected DC samples in the presence of the test substance, thereby resulting in two second factor levels;
(e) Subtracting the first factor level from the second factor level for DCs infected with viruses having a functional K4 protein and for DCs infected with virus having no functional K4 protein to provide two difference factor levels;

(f) Determining, if the difference factor level is positive if a functional K4 was present and negative or zero, when no functional K4 was present. In this case the test substance is an inhibitor of immune factor production by DCs as a result of K4 inhibition.

For example, a virion extract can be made from a virus with high K4 protein activity, as is known for VACV-WR strain, and a plasmid added as substrate for nuclease activity, with or without adding the test substance to analyze whether nuclease activity is inhibited. In one embodiment, 1 μg of plasmid, one μl of virion extract, and x μl of test substance or diluent could be combined in a 50 μl reaction volume as set out above for the nuclease assay. Then, a test substance could be tested for inhibition of IFN-alpha or IFN-lambda induction, or another immune factor, as set out in the examples.

As used herein, an "immune factor" denotes a substance which is involved in initiating, mediating, modulating and/or potentiating an immune response. This includes cytokines such as MIP-1α, MIP-1β, RANTES and IL-6, and interferons (IFNs) such as IFN-α, IFN-β, IFN-λ. While any of these substances may generally be monitored as an indication of the strength of an immune response, in many cases it is sufficient to monitor the level of IFN-α and IFN-λ, to this end. The level of any one or more of these immune factors can be measured by known techniques, for example ELISA.

In preferred embodiments, the test substance/inhibitor of a poxviral K4 protein activity may be chosen from a small molecule, an antibody which specifically binds to a poxviral K4 protein, a peptide, a protein, DNA, RNA or DNA and RNA aptamers, an antisense RNA, a ribozyme, or an siRNA.

A "small molecule" refers to any inorganic, organic or organometallic molecule which is not a biological macromolecule such as a protein or a nucleic acid.

An "antibody" includes full immunoglobulins as well as functional fragments thereof, such as Fab fragments, (Fab)$_2$, Fv fragments (i.e. non covalently associated variable heavy and light chains), single chain Fvs (scFv; i.e. heavy and light variable regions joined to one another by a peptidic linker sequence); bispecific single chain antibodies (i.e. two scFvs tethered to one another via a peptidic linker sequence); and single domain antibodies (dAb). The antibodies and antibody fragments may advantageously be chimeric antibodies, humanized antibodies or fully human antibodies.

A "peptide" refers to a sequence of natural and/or non-natural amino acids joined to one another via amide linkages in the known manner. In the sense used herein, a "peptide" will generally comprise 100 amino acids or less. A "protein" refers to a sequence of natural and/or non-natural amino acids joined to one another via amide linkages in the known manner. In the sense used herein, a "protein" will generally comprise greater than 100 amino acids.

An "RNA or DNA aptamer" refers to short RNA or DNA oligomers of 25-70 nucleotides length with a three-dimensional structure specifically binding K4.

Predictions as to which types of structures are likely to bind to K4 protein, potentially inhibiting its function, can be made based on in silico modelling/docking studies performed with the knowledge of the primary amino acid sequence of the K4 protein (for example SED ID NOs: 2 or 4 or homologs thereof), as well as the three dimensional structure of the test compound, the inhibitory activity of which is to be determined.

According to a further embodiment, the dendritic cell used for assaying an inhibitor of K4 protein activity is a plasmacytoid dendritic cell (pDC). In another embodiment, any cell that responds to ligation of the TLR9 receptor is a potential target for K4 activity. For an example, B cells carry and use the TLR9 receptor and can become less activated by a DNA virus in the presence of K4.

Extending the above, a still further aspect of the present invention provides a process of preparing an inhibitor of a poxviral K4 protein, the method comprising the steps of determining the inhibitor characteristics of a substance according to the method of determining whether or not a substance is an inhibitor of a poxviral K4 protein set out above; and synthesizing or isolating the substance with inhibitor characteristics.

The invention further encompasses uses of the above compositions for treatment of a patient infected with a virus or bacteria expressing K4 protein activity or that contains a K4-like gene. In one embodiment, the virus is a poxvirus. Methods of treatment of patients infected with a virus expressing K4 protein activity or that contains a K4L-like gene are encompassed by the invention. In one embodiment, the method comprises administering an effective amount of an inhibitor of a poxviral K4 protein to a patient.

Enhancement of K4 Protein Activity

Despite the above advantages which can be achieved by reducing or eliminating K4 protein activity, there also exist other scenarios in which an enhancement of existing K4 protein activity, or an addition of K4 protein activity to a virus not previously possessing this activity, can bring a separate set of advantages. Corresponding aspects of the inventions, as well as advantages associated therewith, are set out herein below.

One aspect of the invention in this regard provides a poxviral genome, obtainable by a method comprising providing a poxvirus genome encoding functional K4 protein activity; and mutating the poxvirus genome such that the encoded K4 protein activity is higher than said functional K4 protein activity.

A further aspect of the invention relates to a poxviral genome comprising a gene encoding K4 with enhanced activity.

A further aspect of the invention provides a non-poxviral genome, wherein said non-poxviral genome encodes K4 protein activity. A related aspect of the invention provides a non-poxviral genome, wherein said non-poxviral genome comprises a gene encoding a K4.

Further related aspects provide a vector (preferably a virus or a plasmid vector) encoding a functional K4 protein, such a vector for use as a medicament, and a poxviral K4 protein or a nucleic acid encoding said protein or a functional fragment of said protein or said nucleic acid for use as a medicament. Still further aspects provide any of these substances for use as a medicament for the treatment of a disease characterized by an excessive immune response involving a toll-like receptor 9 (TLR9)-dependent pathway.

A further aspect of the invention provides a poxviral K4 protein or a nucleic acid encoding the protein or a functional fragment of the protein or nucleic acid, a virus vector encoding functional K4 and/or a poxvirus encoding functional K4 for use as a medicament in combination with a vector to enhance expression of the product of a foreign gene and use as a medicament to treat TLR9 pathway dependent disease.

The invention encompasses methods for reducing IFN-α or IFN-λ expression in a host having a TLR9 pathway dependent disease comprising administering a functional K4 protein to the host, particularly wherein the host has an autoimmune disease.

In preferred embodiments, the disease is characterized by an excessive immune response involving a TLR9-dependent pathway, and is chosen from an autoimmune disease, an infectious viral disease, an infectious bacterial disease, an infectious fungal disease, an infectious parasitic disease, a neoplastic disease or sepsis.

In one embodiment, the disease is chosen from systemic lupus erythematosus (SLE), psoriasis, multiple sclerosis (MS), inflammatory bowel disease (IBD) or colitis. In a further embodiment the infectious viral disease is caused by a herpes virus, an adenovirus or a poxvirus. In a further embodiment the infectious parasitic disease is malaria.

In further embodiments the infectious bacterial disease is caused by a mycobacterium.

Certain types of bacterial infections and certain types of neoplasms which thrive in the presence of immune factors, e.g. interferons, can be treated with K4 protein activity, whether this is in the form of poxviruses encoding normal or enhanced levels of K4 protein activity, non-poxviruses into which K4 protein activity has been introduced where it did not previously exist, or in the form of the K4 protein itself. Without being bound by theory, this effect may be due to the tendency of K4 protein activity to depress levels of immune factors such as e.g. interferons, this removing factors on which such diseases would normally thrive. It is understood that such medicaments as set out here may also constitute adjunct therapies to supplement existing therapies of such diseases.

Further aspects of the present invention relating to an enhancement or introduction of K4L gene provide a vector (preferably a virus or a plasmid vector) comprising either (a) a poxviral genome, obtainable by a method comprising: (i) providing a poxvirus genome encoding functional K4 protein activity; and (ii) mutating the poxvirus genome such that the encoded K4 protein activity is higher than said functional K4 protein activity; or (b) a non-poxviral genome, wherein said non-poxviral genome encodes K4 protein activity for use as a medicament for enhancing expression of a foreign protein.

Some gene therapy approaches using gene expression vectors are hampered by insufficient production of foreign protein. Incorporation or enhancement of K4 protein activity in an existing gene therapy vector involving viral delivery vectors may produce higher amounts of foreign antigen before being inactivated by the host immune system. Without being bound by theory, this effect may be attributable to a suppression of immune factors, e.g. cytokines, by K4 protein activity. This suppression of host immune function may allow the vector to persist longer than it otherwise would be able to in the presence of fully active host immune function, thus allowing it more time to express higher amounts of the foreign protein.

According to some aspects of the present invention, K4 protein activity is omitted or reduced, with the effect that the strength of the host immune response to a foreign gene product is heightened. In other aspects, K4 protein activity is introduced or enhanced, with the effect that the viral vector persists longer to produce greater amounts of the foreign protein.

The findings underlying the present invention—based on bidirectional modulation of K4 protein activity—thus provide the skilled person interested in developing and optimizing vaccination approaches as well as vector-driven gene expression with flexible tools allowing very disparate problems to be solved. These findings further allow access to direct disease treatments which did not previously exist and further attest to the flexibility of modulation of K4 protein activity underlying the present invention.

The present invention is further illustrated by the following non-limiting examples and by the accompanying figures, in which

BRIEF DESCRIPTION OF THE FIGURES

FIG. 1A shows the level of IFN-α measured in mice having intact TLR9 function.

FIG. 2 shows the results of experiments in which various CVA and MVA deletion mutants were generated to determine the other poxviral genes besides B19R that influence the host IFN type I and type III response against poxviral infection. The boxes containing a cross drawn in along the schematic representations of various CVA genomes indicate the sequences which have been deleted from the wild-type CVA genome in the various mutant genomes indicated. Of special interest for the present invention are CVA mutants bc12, in which only the B19R gene has been deleted, and bc73, in which both the K4L and B19R genes have been deleted. Of further special interest is MVA mutant-del-K4L with a deleted K4L gene. Comparative studies employing bc12 and bc73 can therefore yield information regarding the immune effect specifically attributable to the K4L gene. The effect of K4L can be studied in this way, i.e. together with B19R deletion, since the B19R gene product can otherwise potentially mask that of the K4L gene product. K2L-K4L or C6L-C8L were replaced by the rpsL-neo counterselection cassette either as a block of genes or separately in the case of K2L, K3L and K4L. B19R was deleted and replaced by a zeocin resistance marker (zeo$^r$) in some of the mutants to facilitate IFN-α detection. Presence of a gene encoding a functional B19 protein is indicated by B19R$^+$. MVA has a truncated B19R gene (B19R-trunc) encoding a non-functional protein.

FIG. 3 shows the results of comparative experiments using bc12 and bc73 CVA variants to infect murine DC. FIG. 3A shows the levels of IFN-α (upper graph) and IFN-λ (lower graph) measured in culture supernatants of murine DC following administration of different amounts of CVA mutant viruses with genomes bc12 and bc73 as shown in FIG. 2.

FIGS. 6A and B depict the effects of an MVA deletion mutant missing the K4L gene (MVA-del-K4L) in the induction of type I and type III interferons in dendritic cells. FIG. 6A shows the levels of IFN-α and FIG. 6B shows the levels of IFN-λ measured in culture supernatants of murine DC following administration of different amounts of MVA-wild-type (-wt) and mutant viruses. Clearly, MVA lacking the K4L gene induced significantly higher amounts of IFN-α and IFN-λ than the MVA-wild-type.

EXAMPLES

Example 1

Correlation of Poxviral Genes with Suppression of IFN-α Production

It was first desired to determine which genes within the poxviral genome may influence the ability of an animal infected by a poxvirus to mount an immune response. An experimental system was designed using mice having and lacking TRL9 gene function, and using mutants of CVA (as a representative poxvirus) including various gene deletions. In one experiment, wild-type CVA having all wild-type gene functions was used to infect dendritic cells (DC) from C57BL/6 mice. In another experiment, DC were infected with a CVA deletion mutant lacking only the B19R gene. In another experiment, DC were infected with a CVA deletion mutant lacking a total of 36 open reading frames including K2L-K4L, but not including B19R. The readout was the level of IFN-α, a higher level being indicative of a more potent immune response. The respective viruses were used to infect the respective DCs at various multiplicities of infection (MOI) as indicated in the legend shown under FIG. 1B.

Figure 1:
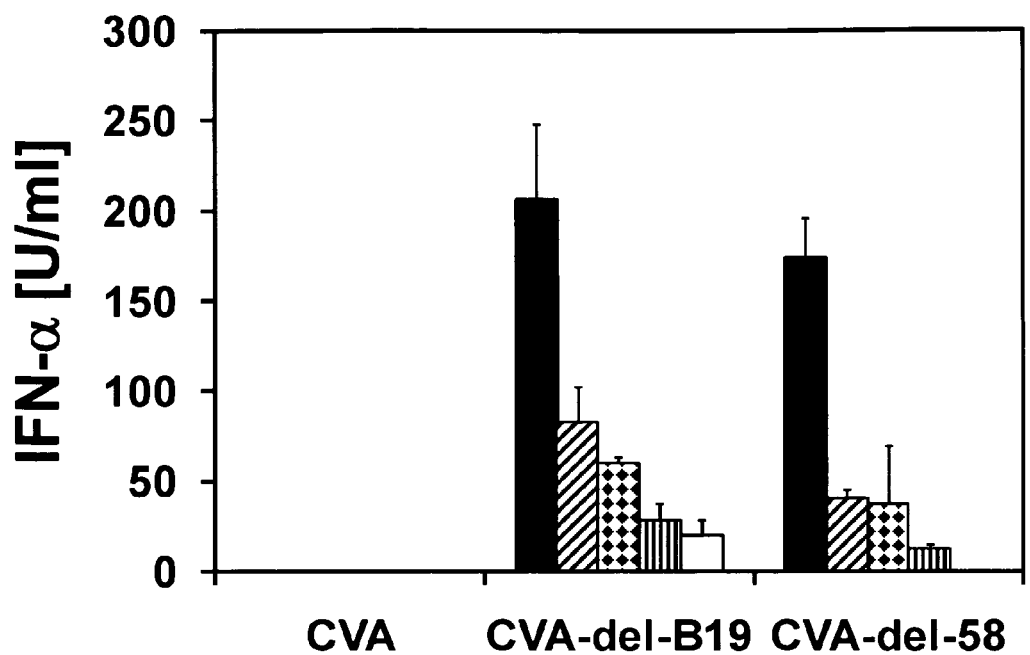
FIGS. 1A and B depict the production of immune factors dependent on the presence of TLR9. The figure shows the results of experiments illustrating the relationship between the presence of the B19R gene in the orthopoxvirus chorioallantois vaccinia virus Ankara (CVA), the presence of TLR9, and the production of the immune factor IFN-α. "CVA" denotes wild-type CVA virus. "CVA-del-B19" denotes CVA virus from which the B19R gene has been deleted. "CVA-del-58" denotes a CVA mutant virus with block deletions of a total of 36 open reading frames, including the genes K2L, K3L and K4L.
FIG. 1B shows the level of IFN-α in knock-out mice lacking TLR9 function. As can be seen in the figure, the level of IFN-α is approximately two-fold higher in DC from mice with intact TLR9 function than in DC from mice lacking this function, indicating the importance of intact TLR9 function in mounting an immune response. Further, it is apparent that intact B19 protein activity is also important, as wild-type CVA (including both B19 and K4 protein activities) produced no detectable IFN-α, while deletion mutants of CVA lacking the B19R gene but retaining the K4L gene led to high levels of IFN-α. At the same time, FIG. 1 indicates that B19R cannot be the sole poxviral gene influencing host immune response, since certain mutants of CVA (CVA-del-58 as shown in the figure) lacking other genes, but not B19R, still led to substantial IFN-α levels. The B19R gene product is thus not attenuating host immune response alone, indicating that the removal of something other than B19R in these mutants caused an enhanced immune reaction as compared to wild-type CVA.
Figure 1:
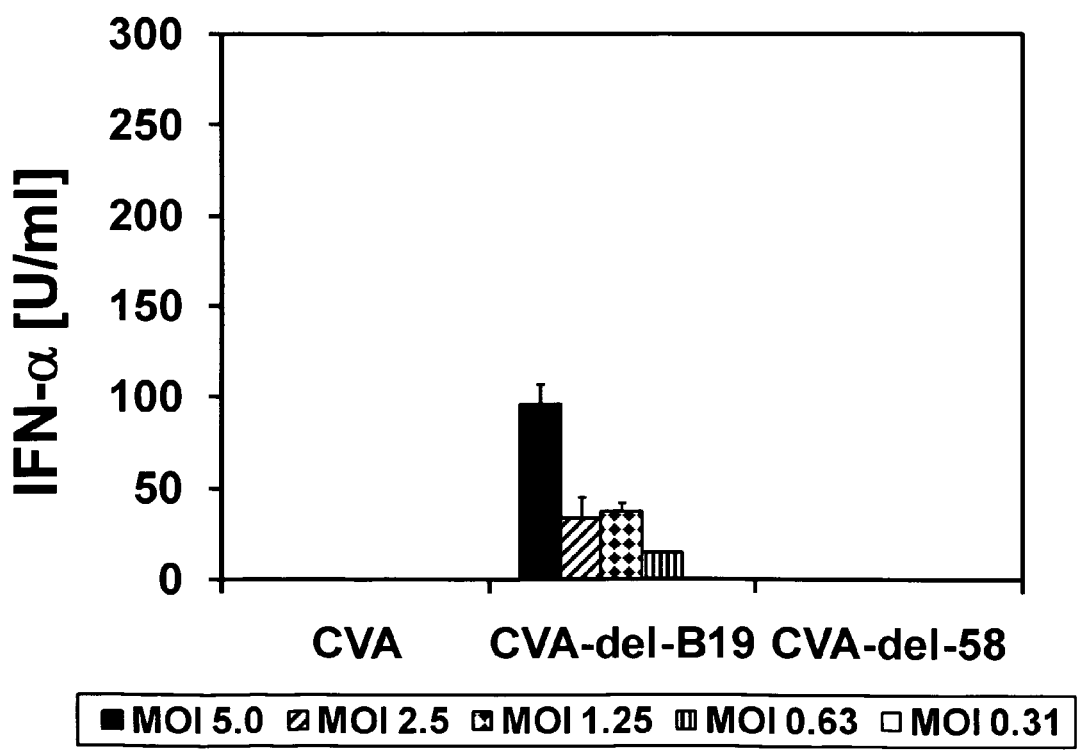

Following infection by the respective virus, supernatants were harvested and analyzed for IFN-α by ELISA. The results are shown in FIG. 1. "CVA" denotes wild-type CVA virus. "CVA-del-B19" denotes CVA virus from which the B19R gene has been deleted. "CVA-del-58" denotes a CVA mutant virus with block deletions of a total of 36 open reading frames, including the genes K2L, K3L and K4L but encoding a functional B19. FIG. 1A shows the level of IFN-α measured in mice having intact TLR9 function. FIG. 1B shows the level of IFN-α in knock-out mice lacking TLR9 function. As can be seen in the figure, the level of IFN-α is approximately twofold higher in DC from mice with intact TLR9 function than in DC from mice lacking this function, suggesting the importance of intact TLR9 function in mounting an immune response. Further, it is apparent that intact B19 function also influences IFN-α levels, as wild-type CVA (including both B19 and K4 protein activities) produced no detectable IFN-α, while deletion mutants of CVA lacking the B19R gene but retaining the K4L gene led to high levels of IFN-α. At the same time, FIG. 1 indicates that B19R cannot be the sole poxviral gene influencing IFN-α secretion by DCs, since certain mutants of CVA (e.g. "CVA-del-58" as shown in the figure) lack other genes instead of B19R, but still led to substantial IFN-α levels. B19R thus does not attenuate host immune response alone, indicating that the removal of something other than the B19R gene in these mutants caused an enhanced immune reaction as compared to wild-type CVA. Furthermore, the strongly enhanced immune reaction of wild-type DCs upon infection with CVA-del-58 compared to CVA was not observed in DCs lacking the TLR9 receptor (FIG. 1B), indicating an inhibition of TLR9-medidated immune enhancement by at least one gene deleted in mutant CVA-del-58.

Example 2

Constructions of CVA Deletion Mutants

Since it was determined above in EXAMPLE 1 that something other than the poxviral B19R gene influences the host system's ability to secrete IFN-α upon poxviral infection of DCs, various poxviral genomes with systematic deletions in various gene regions were constructed to determine what gene this may be. K2L-K4L or C6L-C8L were replaced by the rpsL-neo counter selection cassette either as a block of genes or separately. The B19R gene was deleted and replaced by a zeocin resistance marker in some of the mutants to facilitate IFN-α detection, i.e. so that any potentiation of IFN-α secretion attributable to any other genetic element besides B19 would not be attenuated/masked by B19 IFN-α binding activity.

The construction of the CVA and MVA deletion mutants was performed by BAC recombineering, in the following manner.

Figure 2:
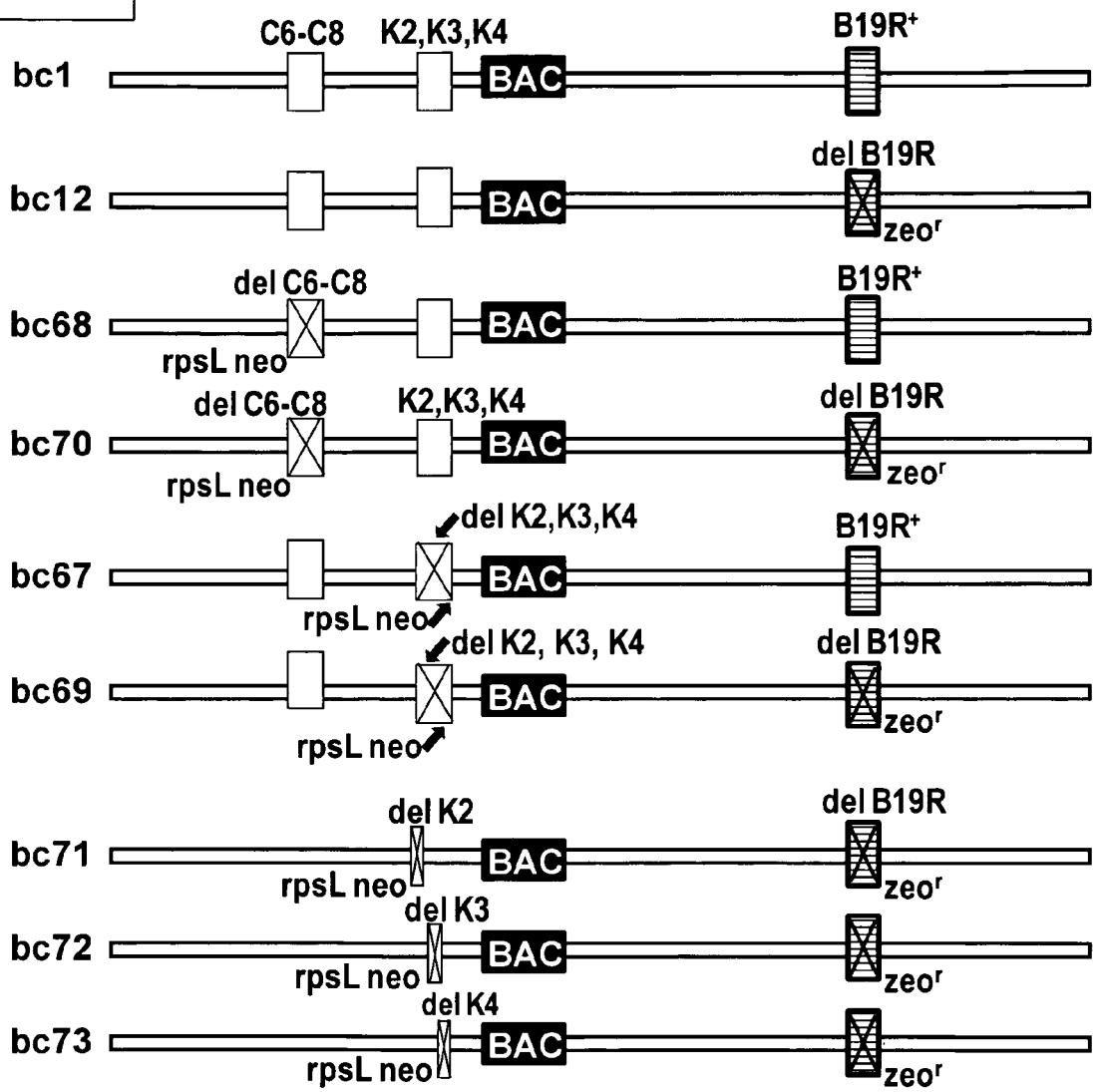
FIG. 2 depicts the generation and genetic analysis of certain CVA and MVA deletion mutants.
Figure 2:
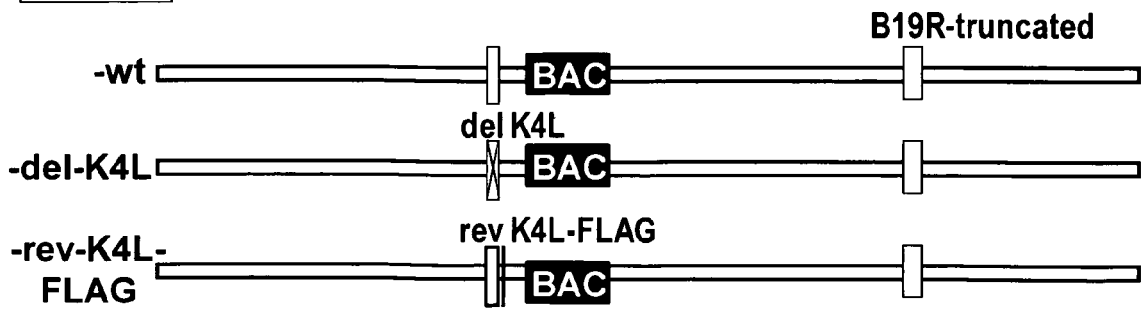
Figure 3A:
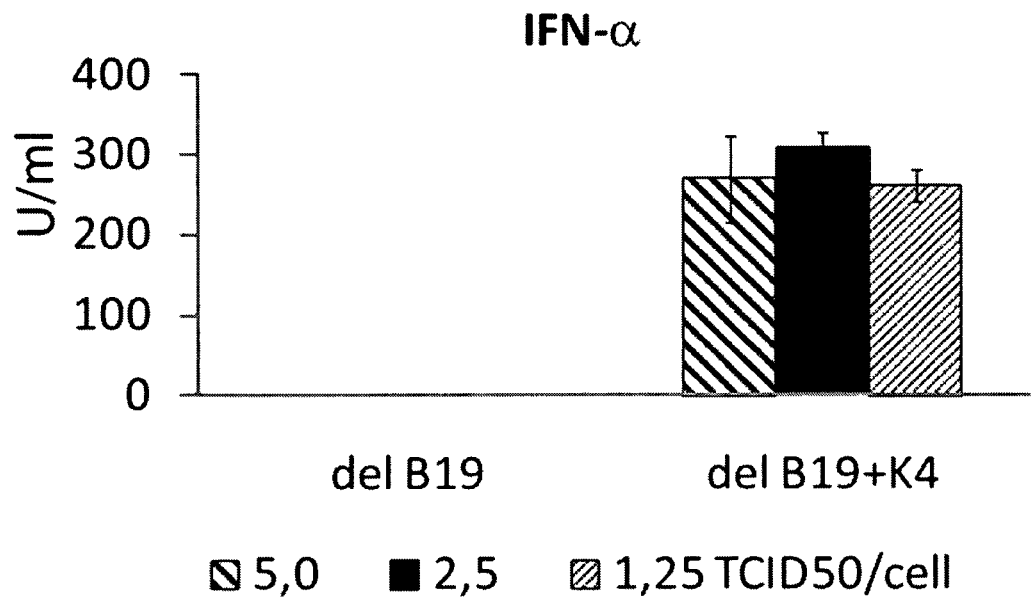
FIGS. 3A and B depict the effects of CVA deletion mutants missing only the B19R gene (bc12) or both B19R and K4L genes (bc73) in the induction of various interferons and cytokines in dendritic cells.
Figure 3A:
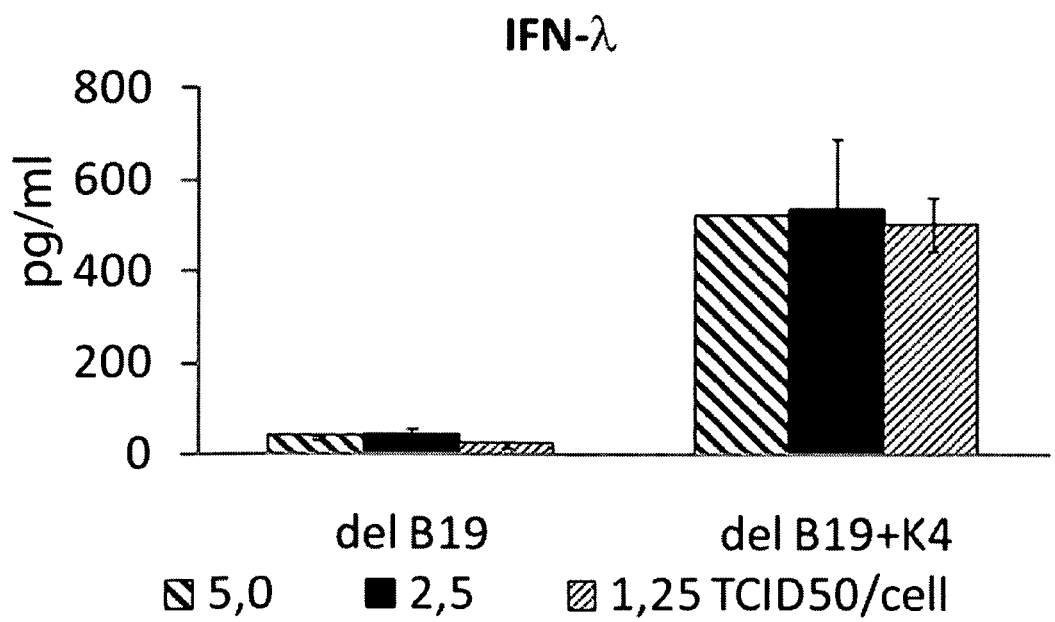
Figure 3B:
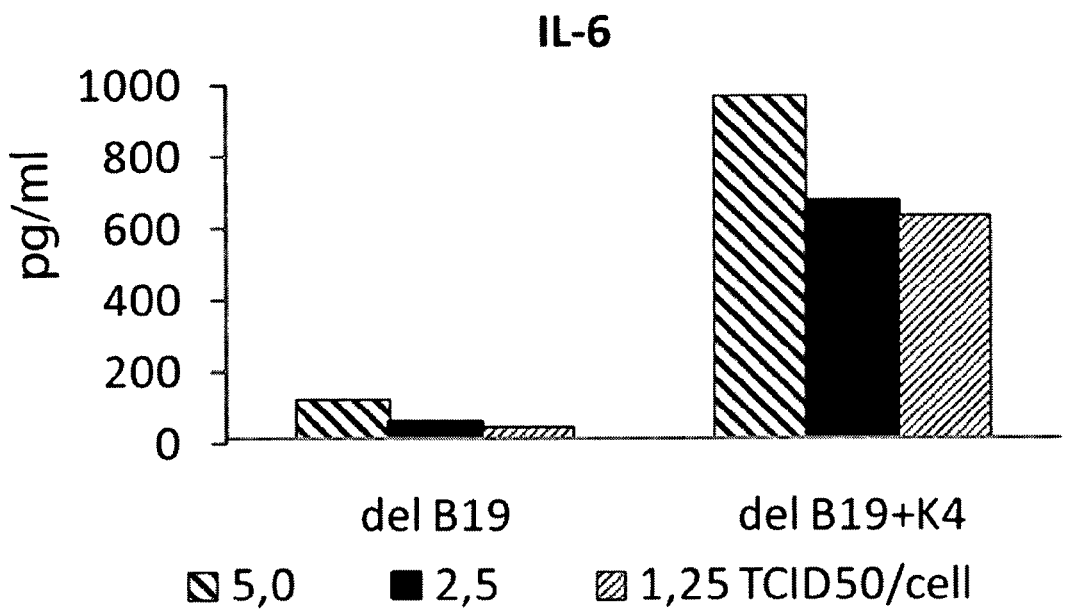
FIG. 3B shows similar experiments in which levels of various cytokines were measured. In each respective graph, the left cluster of data bars (designated "delB19") shows the results obtained infecting with CVA virus bearing the mutant genome bc12 (lacking only the B19R gene), whereas the right cluster of data bars in each respect of graph shows the results obtained infecting with CVA containing the mutant genome bc73 (lacking both B19R and K4L genes). In each graph, the immune stimulatory effect attributable to the deletion of the K4L gene is equivalent to the magnitude of a data bar on the right, minus the corresponding data bar on the left. The results shown in FIG. 3 indicate that deletion of the K4L gene significantly increases the magnitude of immune response as measured by levels of a number of immune factors.
Figure 3B:
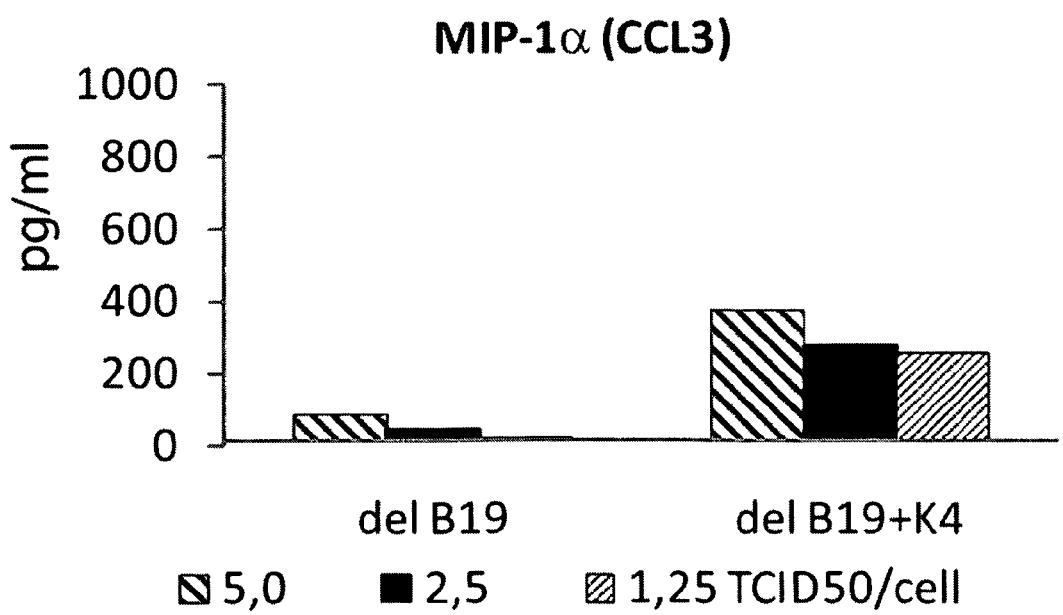
Figure 3B:
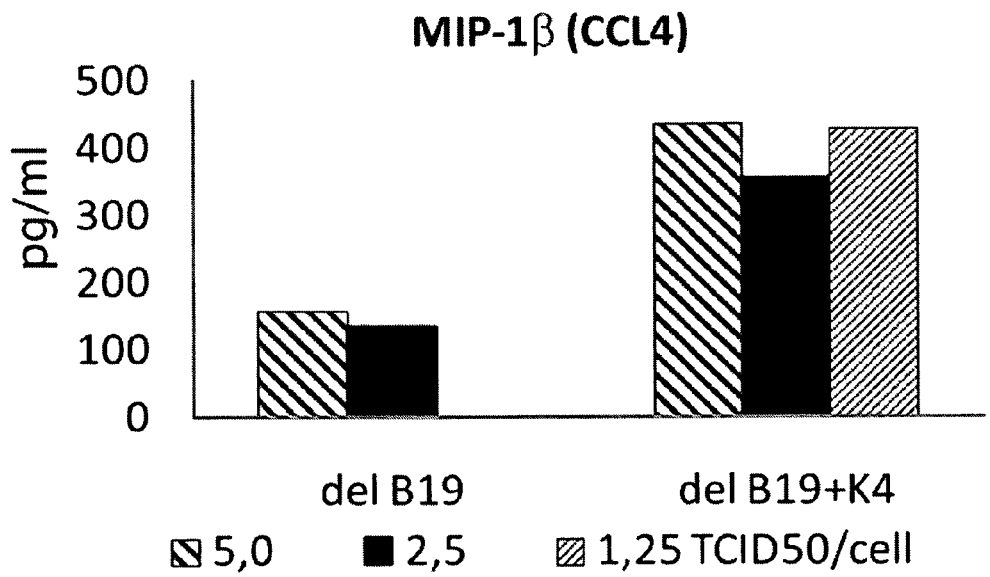
Figure 3B:
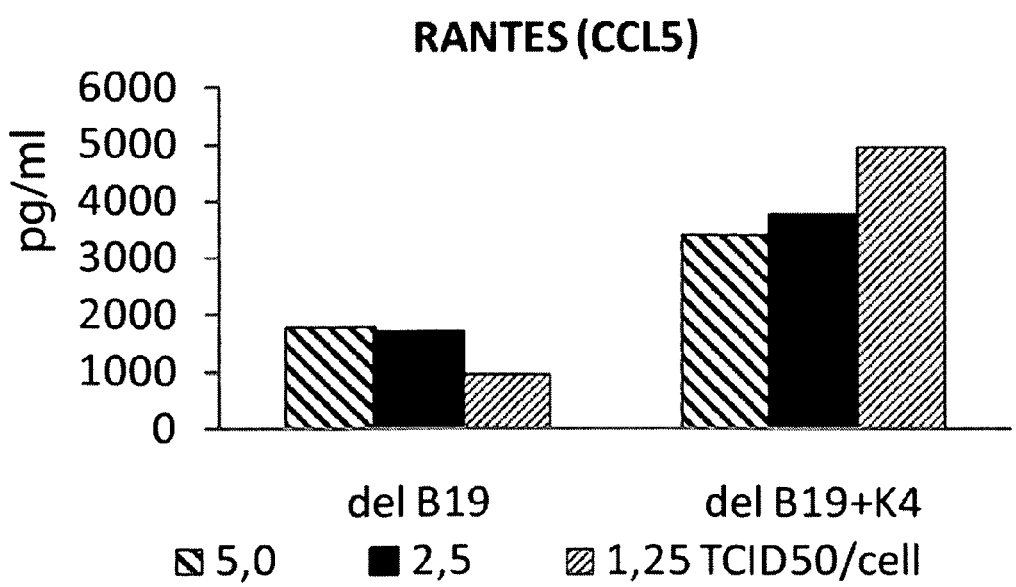

CVA-BAC and MVA-BAC were modified to remove gene segments as indicated in FIG. 2 by allelic exchange in DH10B *E. coli* utilizing the λ Red system for homologous recombination.

Introduction of pKD46 into *E. coli*: Electrocompetent *E. coli* DH10B cells containing the CVA-BAC were electroporated with the pKD46 plasmid and plated on LB plates containing 25 μg/ml of chloramphenicol and 50 μg/ml of ampicillin and incubated overnight at 30° C.

Induction of the λ Red system: DH10B cells containing the BAC of interest and pKD46 encoding the three proteins γ, β, and exo constituting the Red recombinase (Datsenko and Wanner 2000) were propagated at 30° C. to an $OD_{600}$ of 0.3. The λ Red genes were induced by addition of L-arabinose (Merck, Darmstadt, Germany) to a final concentration of 0.4% and incubation at 37° C. for 60 min prior to electroporation.

Introduction of the selection/counterselection cassette: Deletions were obtained by introducing a cassette containing either a zeocin resistance gene ($zeo^r$) the neomycin resistance gene for positive selection and the rpsL gene for counterselection (Reyrat et al. 1998; Wang et al. 2009; Zhang et al. 1998). Briefly, oligonucleotides of 74 bp length (Metabion, Martinsried, Germany) containing the regions of homology to CVA (50 bp) and sequences complementary to the ends of the zeocin or rpsL-neo cassette (24 bp) were used to add homology arms to the 5' and 3' ends of the selection-counterselection cassette by PCR. The PCR products were then electroporated into L-arabinose-induced *E. coli* carrying CVA-BAC and pKD46. Selection was performed on LB plates containing 25 μg/ml of chloramphenicol, 25 μg/ml of kanamycin or zeocin, and 50 μg/ml of ampicillin at 30° C. overnight.

Replacement of rpsL-neo by non-selectable DNA: The rpsL-neo cassette was replaced by electroporation of non-selectable DNA into rpsL-neo-BAC- and pKD46-containing DH10B and induction of homologous recombination as described above. The non-selectable DNA was generated by PCR with long oligonucleotide primers adding 50 bp homology arms at both ends of the non-selectable DNA. To remove the rpsL-neo cassette without a trace, and without any further insertion of DNA, a single-stranded oligonucleotide consisting of 30 bp homology arms at both sides of the insertion site of the rpsL-neo cassette was used. Streptomycin (75 μg/ml) was used for counterselection to obtain rpsL-neo-negative BAC clones. The modified BACs were analyzed by digestion with several restriction enzymes and by direct sequencing of the region containing the introduced modifications. The removal of the selection cassette was further confirmed by nested PCR.

The CVA deletion mutants resulting from the above procedure are shown schematically in FIG. 2. The boxes drawn in along the schematic representations of various CVA genomes indicate the sequences which have been deleted from the wild-type CVA genome in the various mutant genomes indicated. Of special interest for the present invention are CVA mutants bc12, in which only the B19R gene has been deleted, and bc73, in which both the K4L and B19R genes have been deleted. Comparative studies employing bc12 and bc73 may therefore yield information regarding the immune effect specifically attributable to the K4L gene. The effect of the K4L phenotype is studied in this way, i.e. together with B19R deletion, since the B19+phenotype may otherwise potentially mask that of K4L.

Example 3

Effect of K4 on Production of Various Immunologically Relevant Factors

The CVA deletion mutants having genomes bc12 and bc73 as set out in FIG. 2 were then used in a further experiment designed to investigate the effect of K4 protein activity on the production of various immunologically relevant factors such as interferons and a battery of cytokines.

DC generated with FMS-like tyrosine kinase 3 ligand (FL) from wild-type C57BL/6 mice were generated as described (Samuelsson et al. 2008). $5\times10^5$ FL-DC/ml were infected with viruses CVA-del-B19 (bc12) and CVA-del-B19/K4 (bc73) at various MOIs, i.e. at 5, 2.5 and 1.25 $TCID_{50}$/cell in the presence of IL-3 and GM-CSF. Supernatants were harvested from these cell cultures after 18 hr and were analysed by ELISA for IFN-α and IFN-λ or by the following FlowCytomix Multiplex Kits from Bender MedSystems (Campus Vienna Biocenter 2, A-1030 Vienna, Austria): Mouse Th1/Th2 10plex (GM-CSF, IFNc, IL-1a, IL-2, IL-4, IL-5, IL-6, IL-10, IL-17, TNFa) and chemokine 6plex (GM-CSF, MCP-1, MCP-3, MIP-1a, MIP-1b, RANTES). The kits were used according to the manufacturer's instructions as follows:

Preparation of mouse Th1/Th2 and chemokine 6plex cytokine and chemokine standards: Prepare a serial dilution of 1:2 to 1:256 of standard cytokines and chemokines provided in the kits. Don't vortex for mixing! The negative control only contains assay diluent.

Preparation of mixed mouse Th1/Th2 cytokine capture beads: Vigorously vortex each capture bead suspension for a few seconds. Add a 10 μl aliquot of each capture bead for each assay tube into a single tube. Vortex the bead mixture thoroughly.

Mouse Th 1/Th2 cytokine and mouse chemokine 6plex assay procedure: Add 50 μl of the cytokine and chemokine standard silutions and negative control to the respective tubes. Add 50 μl of mixed capture beady to each tube. Add 50 μl of DC supernatant to the respective tubes. Add 50 μl of the mouse Th1/Th2 or mouse chemokine 6plex PE detection reagent to the assay tubes. Incubate for 2 h at room temperature in the dark. Add 1 ml of wash buffer to each assay tube and centrifuge at 200 g for 5 min. Aspirate supernatant. Add 300 μl of wash buffer to each assay tube.

Preparation of cytometer setup beads: Label three 4.5 ml tubes with A, B and C. Add 50 μl of cytometer setup beads to the tubes. Add 50 μl of FITC positive control detector to tube B. Add 50 μl of PE positive control detector to tube C. Incubate for 30 min at room temperature in the dark. Add 450 μl of wash buffer to tube A and 400 μl to tubes B and C.

The samples are then analyzed by flow cytometry using a Bection Dickinson LSR-II.

FIG. 3 shows the concentrations of IFN-α and IFN-λ (FIG. 3A) and for IL-6, MIP-1α and MIP-1β and RANTES (as shown in FIG. 3B) in the supernatants.

FIG. 3A shows the levels of IFN-α (upper graph) and IFN-λ (lower graph) measured in murine DC following administration of different amounts of CVA mutant viruses with genomes bc12 and bc73 as shown in FIG. 2. FIG. 3B shows similar experiments in which levels of various cytokines were measured. In each respective graph, the left cluster of data bars (designated "delB19") shows the results obtained infecting with CVA virus bearing the mutant genome bc12 (lacking only the B19R gene), whereas the right cluster of data bars in each respect of graph shows the results obtained infecting with CVA containing the mutant genome bc73 (lacking both B19R and K4L genes). In each graph, the immune stimulatory effect attributable to deletion of K4 protein activity is equivalent to the magnitude of a data bar on the right, minus the corresponding data bar on the left. The results shown in FIG. 3 indicate that deletion of K4L significantly increases the magnitude of immune response as measured by a number of immune factors.

Example 4

Effect of K4 Protein Activity on Poxviral Pathogenicity In Vivo

Following the above in vitro experiments which suggested that the poxviral K4L gene may influence the ability of a host organism infected with a poxvirus to mount an immune response, it was desired to investigate the in vivo effect of certain of the CVA mutant viruses indicated above. To this end, groups of five 6-8 week old female BALB/c mice were infected intranasally with a 50 μl inoculum containing $10^7$ or $5\times10^7$ $TCID_{50}$ of purified stock of certain CVA mutants per mouse. The mutants used to infect the mice in this experiment were CVA-del-B19 (CVA with the mutant genome indicated as bc12 in FIG. 2), which serves as a reference virus lacking only the B19R gene, and the double-deletion virus CVA-del-K4/B19 (including the mutant genome bc73 as indicated in FIG. 2) to show the effect attributable to the K4L gene. Animals were inspected and weighed daily. The average of the percentage of body weight loss compared to the body weight determined at day 0 of each group is infected for each day post infection. Disease was scored on an arbitrary scale from 0-4 (see table 1 below), the meanings of which are shown in Table 1.

TABLE 1

| Description of disease scores | | |
|---|---|---|
| score | disease status | symptoms |
| 0 | healthy | none |
| 0.5-1.5 | slightly sick | minor or moderately hunched back<br>minor or moderately ruffled fur<br>normal mobility/activity |
| 2.0-2.5 | Sick | clearly hunched back<br>ruffled fur<br>reduced mobility/activity<br>moderate respiratory distress |
| 3.0-3.5 | very sick | strongly hunched posture<br>hedgehog-like walking style<br>coordination problems (walking)<br>strongly ruffled fur<br>significant respiratory distress<br>strongly reduced mobility/activity |
| 4 | moribund | immobile/inactive<br>strongly hunched posture<br>strongly ruffled fur<br>strong respiratory distress<br>paralysis |

Specifically, female BALB/c mice aged 6-8 weeks were purchased from Harlan Winkelmann, Germany. Mice were anaesthetized by ketamine/xylazine injection prior to intranasal infection with either $1\times10^7$ or $5\times10^7$ $TCID_{50}$ of CVA-delB19 and CVAdelB19/K4 mutants diluted in PBS to a final volume of 50 μl per mouse. Animals were weighed and inspected daily and the signs of illness were scored on a scale from 0-4 (see Table 1 above).

The results are shown in FIG. 4. The upper diagram in the figure (FIG. 4A) plots the change in weight measured on each day for two weeks post infection. As is clearly visible from the graph, mice infected with CVA deletion mutants lacking only the B19R gene showed much greater weight loss than mice infected with CVA mutants lacking both B19R and K4L genes. In fact, mice infected with CVA mutants lacking both K4L and B19R genes actually increased somewhat in weight after a week post-infection. During the same time, the mice infected with CVA deletion mutants lacking only the B19R, but in which K4 protein activity was retained, had decreased in weight by up to 30%, indicative of a significantly more severe course of disease in these mice.

Similarly, the lower diagram in FIG. 4 (FIG. 4B) shows that after a week following infection, the disease score of mice having been infected with CVA deletion mutants lacking only the B19R gene but having intact K4 protein activity increased to between 2 and 3. In contrast, the disease score of mice which were infected by CVA deletion mutants lacking both K4 and B19 protein activities never reached a disease score of even 1.

In each case, mice infected with CVA deletion mutants lacking only the B19R gene, but retaining K4 protein activity became significantly more diseased than mice infected with CVA mutants in which both K4L and B19R genes had been deleted, indicating that active K4 protein acts to decrease the host immune response.

Example 5

Effect of K4 Protein Activity on Poxviral Replication

Given the results discussed above, there were reasons to suspect that the activity of the poxviral K4L gene may be a factor in poxviral virulence. The question however remained as to whether K4 protein activity (K4L gene activity) influences poxviral virulence by suppressing the host immune response, or by interfering with the poxviral life cycle, for example by attenuating poxviral replication. In order to investigate this, a further experiment was designed to measure the replication of various poxviruses as well as a CVA deletion mutant lacking the genes K2L, K3L and K4L. The experiments were performed in a variety of cell lines; chicken embryo fibroblasts (CEF), IEC-6 and Vero cells. The indicated cell lines or primary CEF cells were infected in duplicate with 0.05 $TCID_{50}$/cell. Cells were harvested 2 days post infection. Infectious virus titres were determined by standard titration assays on CV-1 cells using the $TCID_{50}$ method. Viral output/ml at day 2 was recorded and plotted. Each data point plotted represented results from single titrations of duplicate samples. The specifics of the method used are indicated below.

Viral replication analysis: For analysis of virus replication and spread, confluent monolayers in 6-well culture plates were infected at 0.05 $TCID_{50}$ per cell using $5\times10^4$ $TCID_{50}$ in 500 μl of DMEM without FCS. After 60 min at 37° C., cells were washed once with DMEM and further incubated with 2 ml of DMEM containing 2% FCS. Cells and supernatant were harvested at the indicated time points, freeze-thawed, sonicated and titrated on CEF cells according to the $TCID_{50}$ method as described (Staib et al. 2004). Briefly, serial dilutions of virus suspensions were plated on CEF cell monolayers grown in 96-well plates as replicates of 8. Cells were fixed with methanol:acetone 50/50 (v/v) five days p.i., and foci of infected cells were visualized by immunostaining. Fixed and permeabilized monolayers were incubated for 30 min with rabbit polyclonal vaccinia virus antibody (Quartett Immunodiagnostika, Berlin, Germany) diluted 1:1000 with PBS/3% FCS followed by incubation with horseradish peroxidase-conjugated polyclonal goat anti-rabbit IgG antibody (Promega, Mannheim, Germany) diluted 1:1000 in PBS/3% FCS for 30 min. After washing, cells were incubated with TMB:PBS substrate solution (Seramun Diagnostica, Heidesee, Germany) for 15 min. Infected wells were identified by purple staining of cells and the infectious titer was calculated using the $TCID_{50}$ method of Spearman and Kärber (Spearman 1908; Kaerber 1931).

Figure 4:
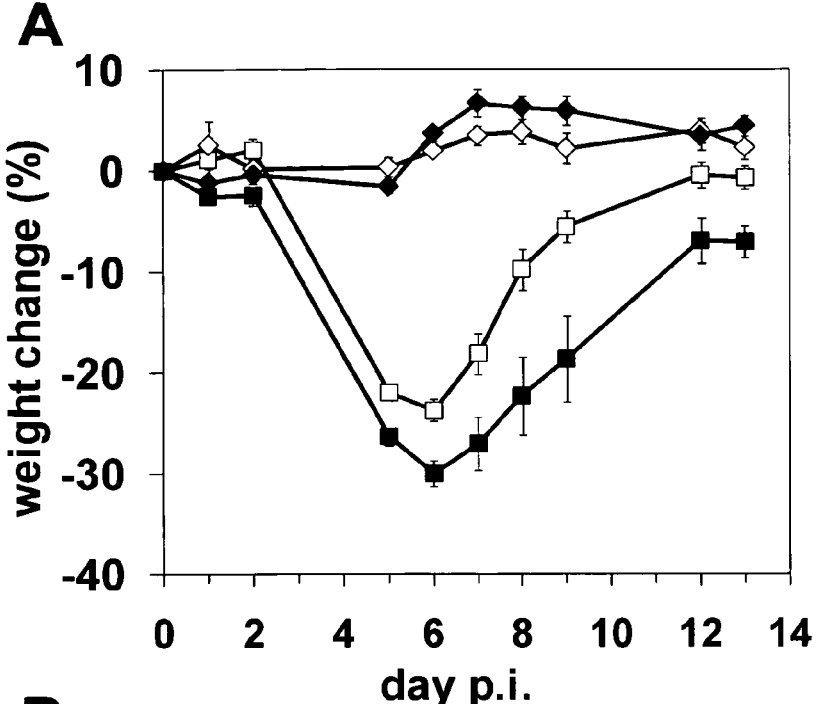
FIGS. 4A and B depict the physiological effect of CVA deletion mutants with and without K4L in vivo. The figure shows results of experiments designed to study the effect of K4L deletion from poxviruses on disease progression in live animals, here BALB-c mice. Data squares show results obtained infecting with CVA mutants missing B19 protein activity but having K4 protein activity. Data diamonds show results obtained infecting with CVA mutants missing both B19 and K4 protein activities. Open symbols indicate inoculation of mice with the lower vial dose of $10^7$ TCID$_{50}$/mouse, whereas solid symbols indicate inoculation with the higher viral dose of $5\times10^7$ TCID$_{50}$/mouse. The two readouts were change in weight (FIG. 4A) and disease score (FIG. 4B). Greater weight loss and higher disease score correlate to a greater severity of disease following infection. As is clear from FIG. 4, by both measures, the mutants missing both B19R and K4L genes caused much less severe disease than mutants missing only the B19R gene. This allows the conclusion that intact K4 protein activity appears important for the pathogenicity of poxviruses. Combined with the results discussed above in FIG. 3, this indicates that a stronger immune response is possible against viruses lacking the K4L gene than against those in which this gene is intact.
Figure 4:
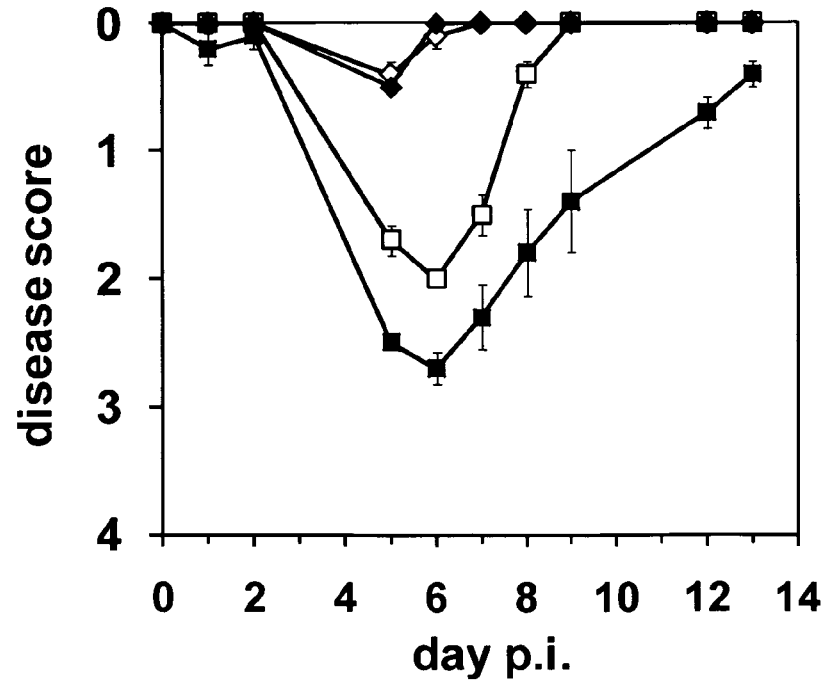
Figure 5:
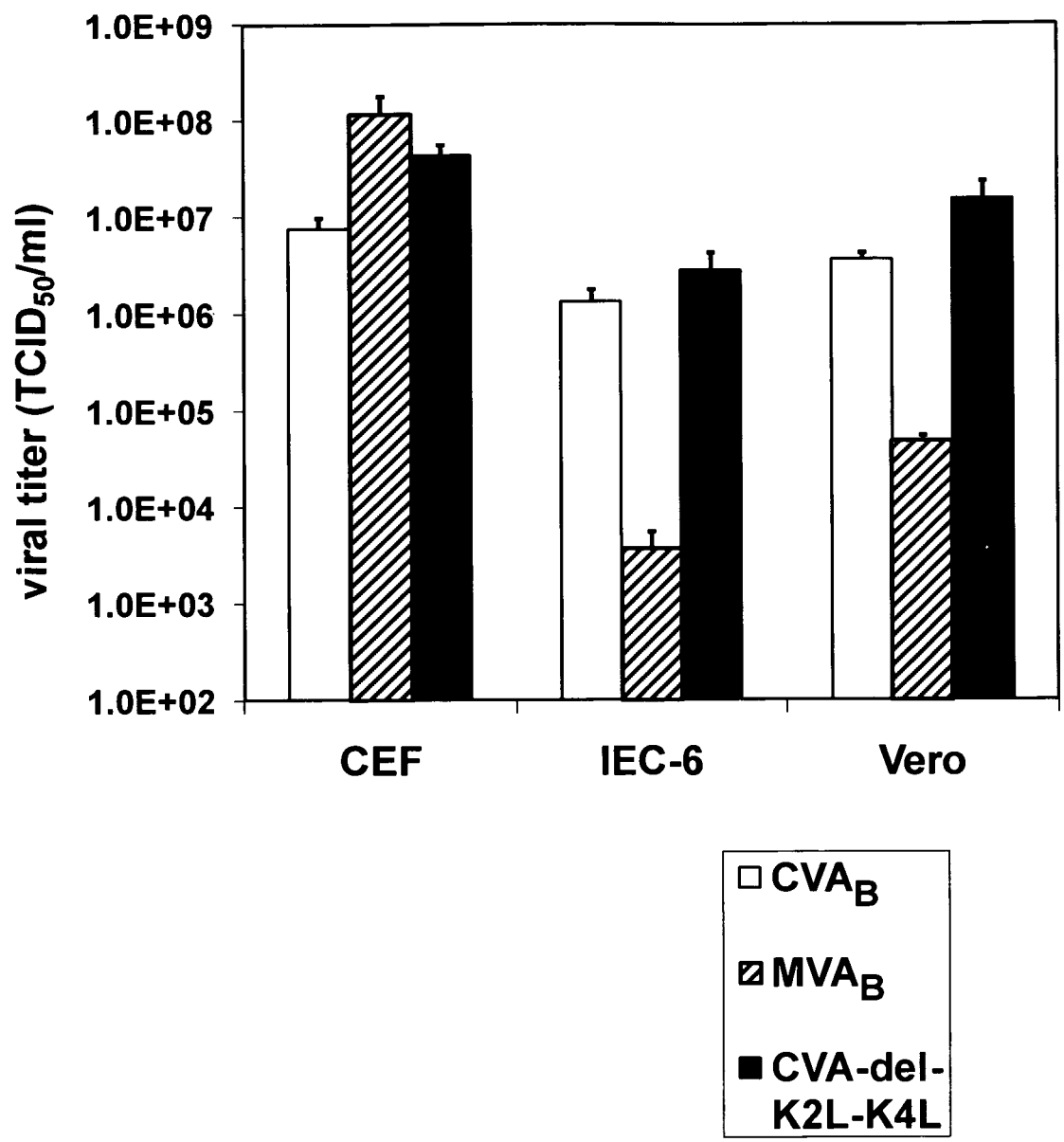
FIG. 5 depicts that K4L is not necessary for replication of poxviruses. CVA and MVA (grey and white data bars, respectively) each have intact K4 protein activity. CVA-del-K2-K4 (bc67 in FIG. 2) lack genes K2L-K4L. In each cell type (CEF, IEC-6, Vero), the replication capacity of the K2L-K4L deletion mutant was at least equivalent to that of wild-type CVA, and in IEC-6 and Vero cells, the K2-K4 deletion mutants showed a higher replication capacity than MVA. This indicates that the lower pathogenicity seen in FIG. 4 for K4 deletion mutants was not due to a reduced ability of the virus to replicate, i.e. that deletion of the K4L gene did not impair the virus' replication in cell culture.

The results are shown in FIG. 5. CVA-del-K2-K4 (bc67 in FIG. 2) lacks genes K2L-K4L. In each cell type (CEF, IEC-6, Vero), the replication capacity of the K2L-K4L deletion mutant was at least equivalent to that of wild-type CVA, and in IEC-6 and Vero cells, wild-type CVA and the K2-K4 deletion mutants showed higher replication than MVA. This indicates that the lower pathogenicity seen in FIG. 4 for K4L deletion mutants was not due to an inability of the virus to replicate, i.e. that deletion of the K4L gene did not abrogate viral replication.

Example 6

Effect of K4 Deletion from the MVA Genome on Production of Type I and Type III Interferons FL-DCs from wild-type C57BL/6 mice were generated as described (Samuelsson et al. 2008). $5 \times 10^5$ FL-DC/ml were infected with viruses MVA-wt, MVA-del-K4L and MVA-rev-K4L-FLAG at various MOIs, i.e. at 5, 2.5 and 1.25, 0.6 and 0.3 $TCID_{50}$/cell. Supernatants were harvested from these cell cultures after 18 hr and were analysed by ELISA for IFN-α and IFN-λ.

Figure 6:
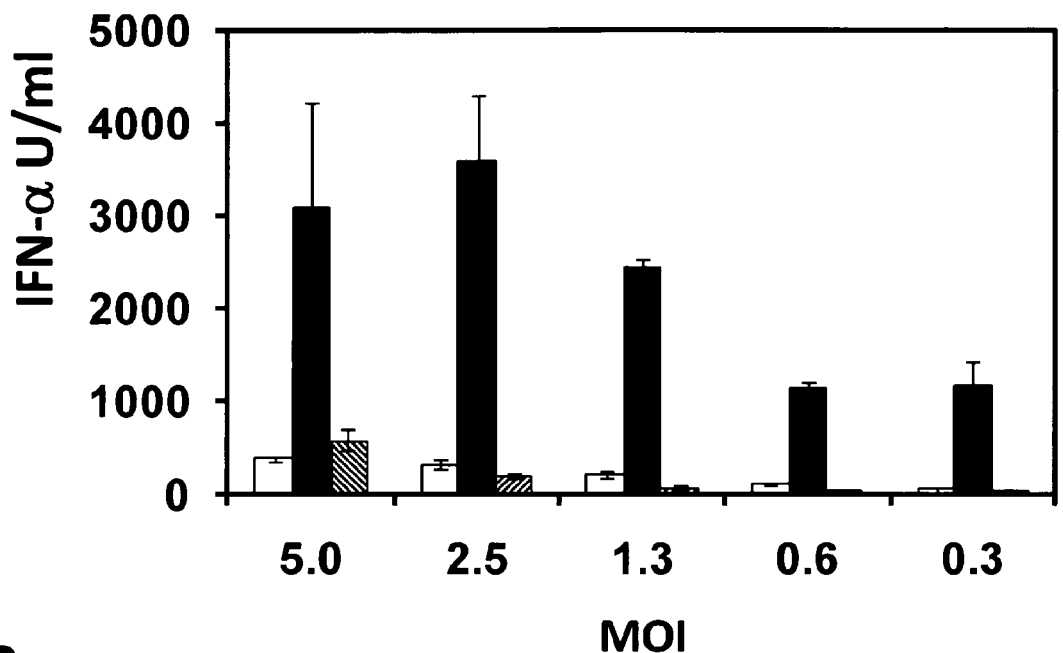
FIG. 6 shows the results of comparative experiments using MVA-wt and -MVA-del-K4L as well as an MVA revertant with a re-inserted K4L gene encoding a FLAG-tagged K4 protein.
Figure 6:
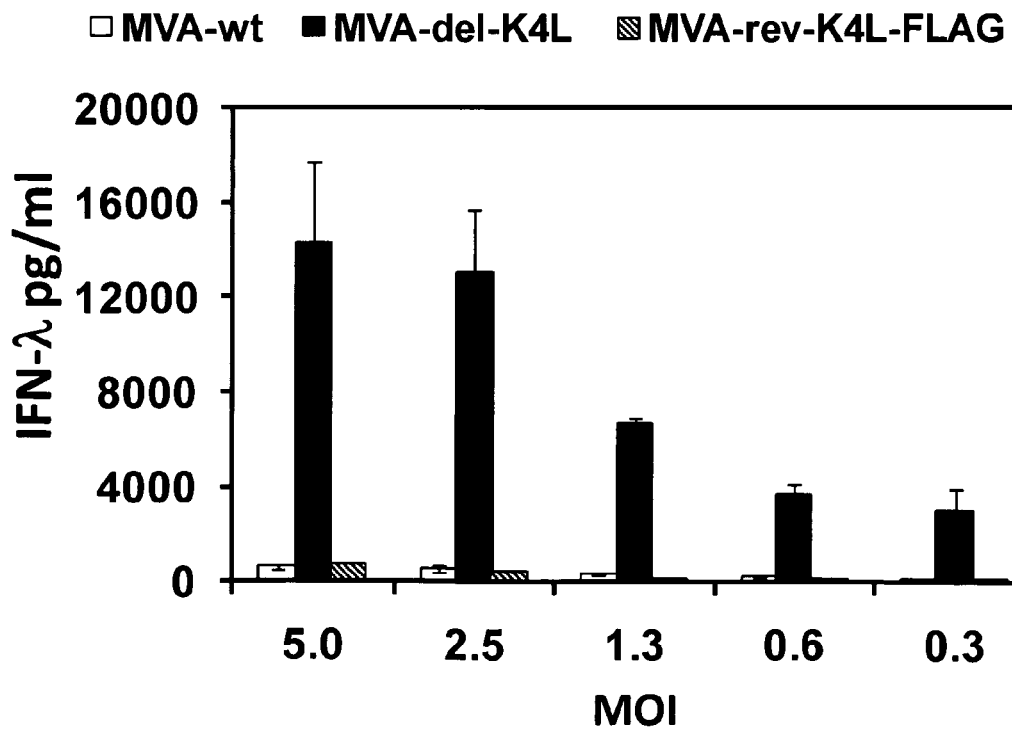

FIG. 6 shows the concentrations of IFN-α (A) and IFN-λ (B) measured in murine DC following administration of different amounts of MVA mutant viruses as described above. In each graph, the immune stimulatory effect attributable to deletion of K4 protein activity is equivalent to the magnitude of the grey filled data bar, minus the corresponding data bar for MVA-wt on the left or minus the corresponding data bar for MVA-rev-K4L-FLAG. The results shown in FIG. 6 indicate that deletion of K4L significantly increases the magnitude of IFN-α and IFN-λ secretion from DCs induced by MVA. FIG. 6 further shows that a K4 protein with a C-terminal FLAG-tag is as inhibitory as the wild-type K4 version without FLAG tag in MVA-wt since induction of IFN-α and IFN-λ by MVA-wt and MVA-rev-K4L-FLAG is indistinguishable.

References

Antoine G., F. Scheiflinger, F. Dorner, and F. G. Falkner (1998) The complete genomic sequence of the modified vaccinia Ankara strain: comparison with other orthopoxviruses. *Virology* 244:365-396.

Datsenko K. A. and B. L. Wanner (2000) One-step inactivation of chromosomal genes in *Escherichia coli* K-12 using PCR products. *Proc. Natl. Acad. Sci. U.S.A* 97:6640-6645.

Eckert D., O. Williams, C. A. Meseda, and M. Merchlinsky (2005) Vaccinia virus nicking-joining enzyme is encoded by K4L (VACWR035). *J. Virol.* 79:15084-15090.

Goebel S. J., G. P. Johnson, M. E. Perkus, S. W. Davis, J. P. Winslow, and E. Paoletti (1990) The complete DNA sequence of vaccine virus. *Virology* 179:247-263.

Kaerber G. (1931) Beitrag zur kollektiven Behandlung pharmakologischer Reihenversuche. *Arch. Exp. Pathol. Pharmakol.* 162:480-483.

Kotwal G. J. and M. R. Abrahams (2004) Growing poxviruses and determining virus titer. *Methods Mol. Biol.* 269:101-112.

Reyrat J. M., V. Pelicic, B. Gicquel, and R. Rappuoli (1998) Counterselectable markers: untapped tools for bacterial genetics and pathogenesis. *Infect. Immun.* 66:4011-4017.

Rosel J. L., P. L. Earl, J. P. Weir, and B. Moss (1986) Conserverd TAAATG sequence at the transcriptional and translational initiation sites of vaccinia virus late genes deduced by structural and functional analysis of the HindIII H genome fragment. *J. Virol.* 60:436-449.

Samuelson C., J. Hausmann, H. Lauterbach, M. Schmidt, S. Akira, H. Wagner, P. Chaplin, M. Suter, M. O'Keeffe, and H. Hochrein (2008) Survival of lethal poxvirus infection in mice depends on TLR9, and therapeutic vaccination provides protection. *J. Clin. Invest.* 118:1776-1784.

Spearman C. (1908) The method of "right and wrong cases" ("constant stimuli") without Gauss's formulae. *Brit. J. Psychol.* 2:227-242.

Staib C., I. Drexler, and G. Sutter (2004) Construction and isolation of recombinant MVA. *Methods Mol. Biol.* 269:77-100.

Symons J. A., A. Alcamini, and G. L. Smith (1995) Vaccinia virus encodes a soluble type I interferon receptor of novel structure and broad species specificity. *Cell* 81:551-560.

Wang S., Y. Zhao, M. Leiby, and J. Zhu (2009) A new positive/negative selection scheme for precise BAC recombineering. *Mol. Biotechnol.* 42:110-116

Zhang Y., F. Buchholz, J. P. Muyrers, and A. F. Stewart (1998). A new logic for DNA engineering using recombination in *Escherichia coli*. *Nat. Genet.* 20:123-128.

The invention claimed is:

1. A recombinant poxvirus encoding a foreign viral or human tumor associated antigen and having reduced K4 protein activity relative to wild-type K4 protein activity.

2. The recombinant poxvirus of claim 1, wherein the poxvirus has no K4 protein activity.

3. The recombinant poxvirus of claim 2, wherein the poxvirus does not contain a K4L gene.

4. The recombinant poxvirus of claim 1, further having reduced B19 protein activity relative to wild-type B19 protein activity.

5. The recombinant poxvirus of claim 4, wherein the poxvirus is a vaccinia virus (VACV) or a chorioallantois vaccinia virus Ankara (CVA).

6. The recombinant poxvirus of claim 5, wherein the vaccinia virus is a modified vaccinia virus Ankara (MVA).

7. A recombinant poxvirus having reduced K4 protein activity relative to wild-type K4 protein activity and reduced B19 protein activity relative to wild-type B19 protein activity.

8. The recombinant poxvirus of claim 7, wherein the poxvirus has no K4 protein activity.

9. The recombinant poxvirus of claim 8, wherein the poxvirus does not contain a K4L gene.

10. The recombinant poxvirus of claim 7, wherein the poxvirus has no B19 protein activity.

11. The recombinant poxvirus of claim 10, wherein the poxvirus does not contain a B19 gene.

12. The recombinant poxvirus of claim 7, wherein the poxvirus is a VACV or a CVA.

13. The recombinant poxvirus of claim 11, wherein the poxvirus is a VACV or a CVA.

14. A modified vaccinia virus Ankara (MVA) having reduced K4 protein activity relative to wild-type K4 protein activity.

15. The MVA virus of claim 14, having no K4 protein activity.

16. The MVA virus of claim 15, wherein the virus does not contain a K4L gene.

17. An immunogenic composition comprising the recombinant poxvirus of claim 1 and a pharmaceutically acceptable carrier.

18. An immunogenic composition comprising the recombinant poxvirus of claim 7 and a pharmaceutically acceptable carrier.

19. An immunogenic composition comprising the modified MVA of claim 14 and a pharmaceutically acceptable carrier.

20. A method of enhancing an immune response to a vaccination regimen, comprising administering the immunogenic composition of claim 17.

21. The method of claim 20, wherein the enhanced immune response is increased production of interferon-alpha (IFNα) or interferon-lambda (IFNλ).

22. A method of enhancing an immune response to a vaccination regimen, comprising administering the immunogenic composition of claim 18.

23. The method of claim 22, wherein the enhanced immune response is increased production of interferon-alpha (IFNα) or interferon-lambda (IFNλ).

24. A method of enhancing an immune response to a vaccination regimen, comprising administering the immunogenic composition of claim 19.

25. The method of claim 24, wherein the enhanced immune response is increased production of interferon-alpha (IFNα) or interferon-lambda (IFNλ).

26. A method for generating a poxvirus having reduced K4 protein activity and reduced B19 protein activity, comprising:
    introducing a mutation into a K4 gene of a poxvirus, wherein the resulting mutated poxvirus has reduced K4 protein activity; and
    introducing a mutation into a B19 gene of a poxvirus, wherein the resulting mutated poxvirus has reduced B19 protein activity.

27. The method of claim 26, wherein the poxvirus is a VACV or a CVA.

28. A method for generating a modified vaccinia virus Ankara (MVA) having reduced K4 protein activity, comprising introducing a mutation into a K4 gene of the MVA, wherein the resulting mutated MVA has reduced K4 protein activity.

* * * * *